United States Patent
Yuan-Huffman et al.

(10) Patent No.: US 9,080,043 B2
(45) Date of Patent: Jul. 14, 2015

(54) COMPOSITIONS OF VISCOELASTIC SURFACTANT AND HYDROPHOBICALLY MODIFIED POLYMER AS AQUEOUS THICKENERS

(75) Inventors: Qingwen Wendy Yuan-Huffman, Belle Mead, NJ (US); Klin Aloysius Rodrigues, Signal Mountain, TN (US); Jian Zhou, Danbury, CT (US); Stuart Peter Robert Holt, Chicago, IL (US); Elliot Isaac Band, Pleasantville, NY (US)

(73) Assignee: AKZO NOBEL CHEMICALS INTERNATIONAL B.V., Amersfoort (NL)

(*) Notice: Subject to any disclaimer, the term of this patent is extended or adjusted under 35 U.S.C. 154(b) by 0 days.

(21) Appl. No.: 13/995,062
(22) PCT Filed: Dec. 15, 2011
(86) PCT No.: PCT/EP2011/072861
§ 371 (c)(1),
(2), (4) Date: Jun. 17, 2013
(87) PCT Pub. No.: WO2012/080382
PCT Pub. Date: Jun. 21, 2012

(65) Prior Publication Data
US 2013/0274170 A1  Oct. 17, 2013

Related U.S. Application Data

(60) Provisional application No. 61/423,710, filed on Dec. 16, 2010.

(30) Foreign Application Priority Data

Apr. 6, 2011  (EP) .................................... 11161261

(51) Int. Cl.
*C11D 1/75* (2006.01)
*C11D 3/37* (2006.01)
(Continued)

(52) U.S. Cl.
CPC ............... *C08L 39/00* (2013.01); *A61K 8/8111* (2013.01); *A61K 8/8147* (2013.01); *A61K 8/84* (2013.01);
(Continued)

(58) Field of Classification Search
CPC .......... C11D 1/75; C11D 3/37; C11D 3/3746; C11D 3/3757; C11D 3/3769; C11D 3/3788; C09K 8/60; C09K 8/88
USPC .......... 510/433, 475, 499, 503; 507/129, 221, 507/224, 225; 166/259
See application file for complete search history.

(56) References Cited

U.S. PATENT DOCUMENTS 2,396,278 A  3/1946 Lind
2,486,921 A  11/1949 Byerly
(Continued)

FOREIGN PATENT DOCUMENTS

EP  0250943 A2  1/1988
EP  0875557 A2  11/1998
(Continued)

OTHER PUBLICATIONS

International Search Report and Written Opinion of corresponding Patent Application No. PCT/EP2011/072861, mailed Apr. 5, 2012.
(Continued)

*Primary Examiner* — Brian P Mruk
(74) *Attorney, Agent, or Firm* — Matthew D. Kellam

(57) ABSTRACT

An aqueous viscoelastic composition is provided comprising at least one viscoelastic surfactant, and at least one hydrophobically modified polymer, which is formed from polymerization of ethylenically unsaturated monomers; has a number average molecular weight of from 1,000 to 100,000 Da; and to a level of at least 0.1 mole %, based on the amount of monomer units in the polymer, contains monomeric units each covalently bonded to a pendant, optionally alkoxylated, hydrocarbyl group having from 6 to 40 carbon atoms, said pendant, optionally alkoxylated, hydrocarbyl group being connected to the backbone of said hydrophobically modified polymer via a non-ester containing linking group.

27 Claims, 6 Drawing Sheets

(51) Int. Cl.

| | | |
|---|---|---|
| C09K 8/60 | (2006.01) | |
| C09K 8/88 | (2006.01) | |
| C08L 39/00 | (2006.01) | |
| A61Q 19/00 | (2006.01) | |
| C09K 8/68 | (2006.01) | |
| A61Q 5/02 | (2006.01) | |
| A61Q 5/12 | (2006.01) | |
| A61Q 9/02 | (2006.01) | |
| A61Q 19/10 | (2006.01) | |
| C11D 1/94 | (2006.01) | |
| C11D 17/00 | (2006.01) | |
| A61K 8/81 | (2006.01) | |
| A61K 8/84 | (2006.01) | |
| A61K 8/87 | (2006.01) | |
| A61Q 5/00 | (2006.01) | |
| C08L 33/10 | (2006.01) | |
| C08L 33/26 | (2006.01) | |
| E21B 43/26 | (2006.01) | |
| C11D 1/29 | (2006.01) | |
| C11D 1/92 | (2006.01) | |

(52) U.S. Cl.
CPC ... *A61K 8/87* (2013.01); *A61Q 5/00* (2013.01); *A61Q 5/02* (2013.01); *A61Q 5/12* (2013.01); *A61Q 9/02* (2013.01); *A61Q 19/00* (2013.01); *A61Q 19/10* (2013.01); *C08L 33/10* (2013.01); *C08L 33/26* (2013.01); *C09K 8/604* (2013.01); *C09K 8/68* (2013.01); *C09K 8/88* (2013.01); *C11D 1/94* (2013.01); *C11D 3/3765* (2013.01); *C11D 17/003* (2013.01); *E21B 43/26* (2013.01); *C09K 2208/30* (2013.01); *C11D 1/29* (2013.01); *C11D 1/92* (2013.01)

(56) References Cited

U.S. PATENT DOCUMENTS

| | | | |
|---|---|---|---|
| 2,486,922 A | 11/1949 | Strain | |
| 2,528,378 A | 10/1950 | Mannheimer et al. | |
| 3,332,880 A | 7/1967 | Kessler et al. | |
| 3,929,678 A | 12/1975 | Laughlin et al. | |
| 4,432,881 A | 2/1984 | Evani | |
| 4,524,175 A | 6/1985 | Stanley, Jr. | |
| 4,541,935 A | 9/1985 | Constien et al. | |
| 4,814,096 A | 3/1989 | Evani | |
| 5,425,806 A | 6/1995 | Doolan et al. | |
| 5,566,760 A | 10/1996 | Harris | |
| 5,916,967 A | 6/1999 | Jones et al. | |
| 6,020,407 A | 2/2000 | Campbell et al. | |
| 7,084,095 B2 | 8/2006 | Lee et al. | |
| 2002/0042453 A1 | 4/2002 | Iliopoulos et al. | |
| 2003/0134751 A1 | 7/2003 | Lee et al. | |
| 2004/0097385 A1 | 5/2004 | Chen et al. | |
| 2005/0119401 A1 | 6/2005 | Bavouzet et al. | |
| 2006/0128597 A1 | 6/2006 | Chen et al. | |
| 2006/0142501 A1 | 6/2006 | Badiger et al. | |
| 2006/0147406 A1 | 7/2006 | Yerby et al. | |
| 2007/0111896 A1 | 5/2007 | Knox et al. | |
| 2007/0281869 A1 | 12/2007 | Drochon et al. | |
| 2009/0023616 A1 | 1/2009 | Couillet et al. | |
| 2009/0107681 A1* | 4/2009 | Hough et al. | 166/308.3 |
| 2009/0111716 A1 | 4/2009 | Hough et al. | |
| 2009/0186796 A1* | 7/2009 | Gomez Ruiz et al. | 510/237 |
| 2011/0053807 A1* | 3/2011 | Panga et al. | 507/115 |
| 2011/0053812 A1 | 3/2011 | Ezell et al. | |
| 2013/0266531 A1 | 10/2013 | Yuan-Huffman et al. | |

FOREIGN PATENT DOCUMENTS

| | | |
|---|---|---|
| EP | 2018890 A2 | 1/2009 |
| GB | 2383355 A | 6/2003 |
| WO | WO03/056130 A1 | 7/2003 |
| WO | WO2005/023970 A1 | 3/2005 |
| WO | WO2009/036160 A1 | 3/2009 |
| WO | WO2011/062805 A1 | 5/2011 |

OTHER PUBLICATIONS

European Search of corresponding Patent Application No. 11161261.0, mailed Jul. 19, 2011.
International Search and Written Opinion of related Patent Application No. PCT/EP2011/072863, mailed Aug. 2, 2013.
J.E. Glass, "Polymers in Aqueous Media" Performance Through Association, Advances in Chemistry Series 223, Aug. 30, 1987, pp. 343-366.
H. Hoffmann, et al, "Influence of Ionic Surfactants on the Viscoelastic Properties of Zwitterionic Surfactant Solutions", Langmuir, 8, pp. 2140-2146, 1992.
B. Magny et al, "Mixed Micelles Formed by Cationic Surfactants and Anionic Hydrophobically Modified Polyelectrolytes", Langmuir, 10, pp. 3180-3187, 1994.
H.A. Barnes et al, "An Introduction to Rheology", Elsevier, Amsterdam, pp. 45-54, 1993.
H. Hoffmann et al, "The Rheological Behaviour of Different Viscoelastic Surfactant Solutions", Tenside Surf. Det. 31, pp. 389-400, 1994.
Pierre-Gilles de Gennes, "Scaling Concepts in Polymer Physics", pp. 76-77, Cornell University Press, Ithaca and London, 1979.
Dai et al., "Dynamic Light Scattering of Semidilute Hydrophobically Modified Alkali-Soluble Emulsion Solutions with Different Lengths of Poly(ethylene oxide) Spacer Chain," Journal of Polymer Science: Part B: Polymer Physics, vol. 43, Wiley Periodicals, Inc., pp. 3288-3298, © 2005.

* cited by examiner

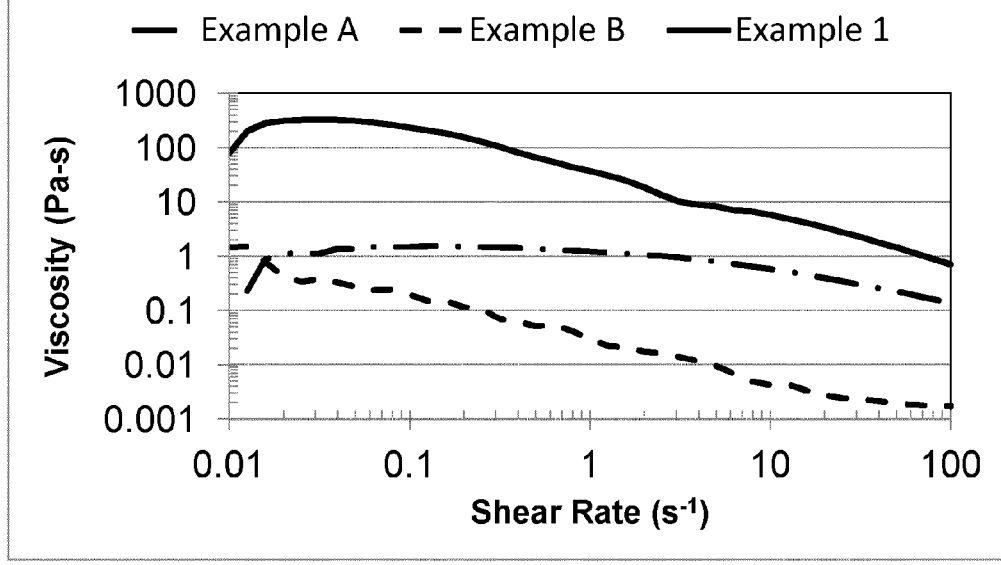
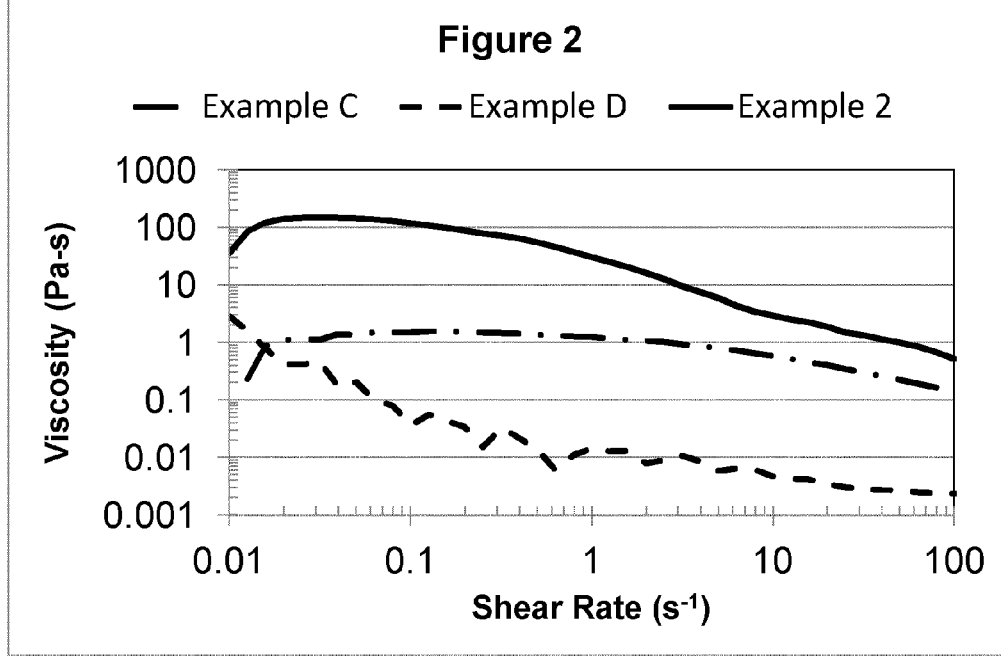

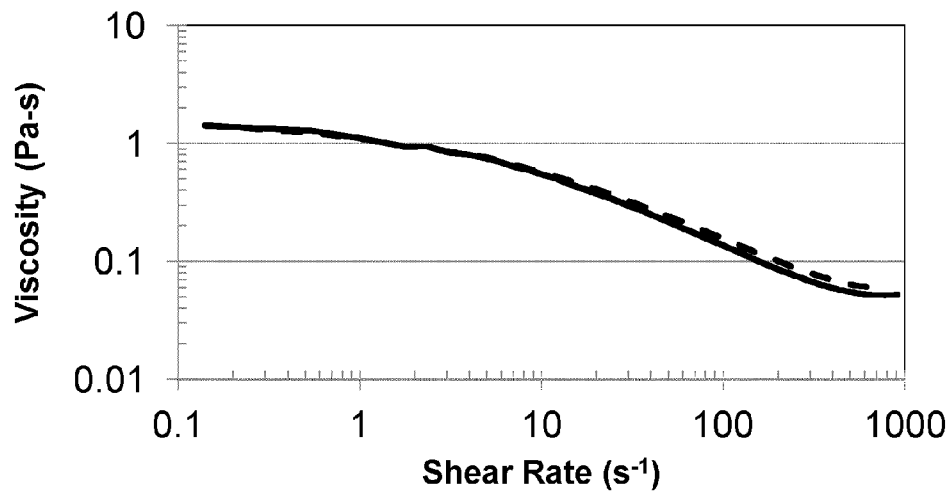
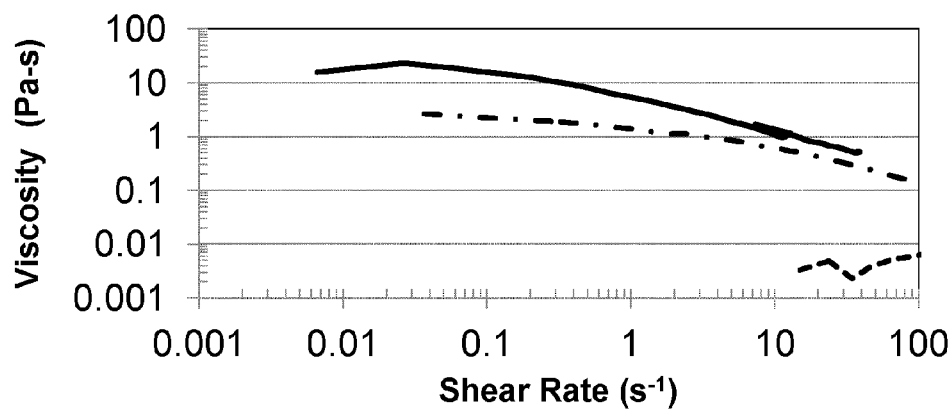

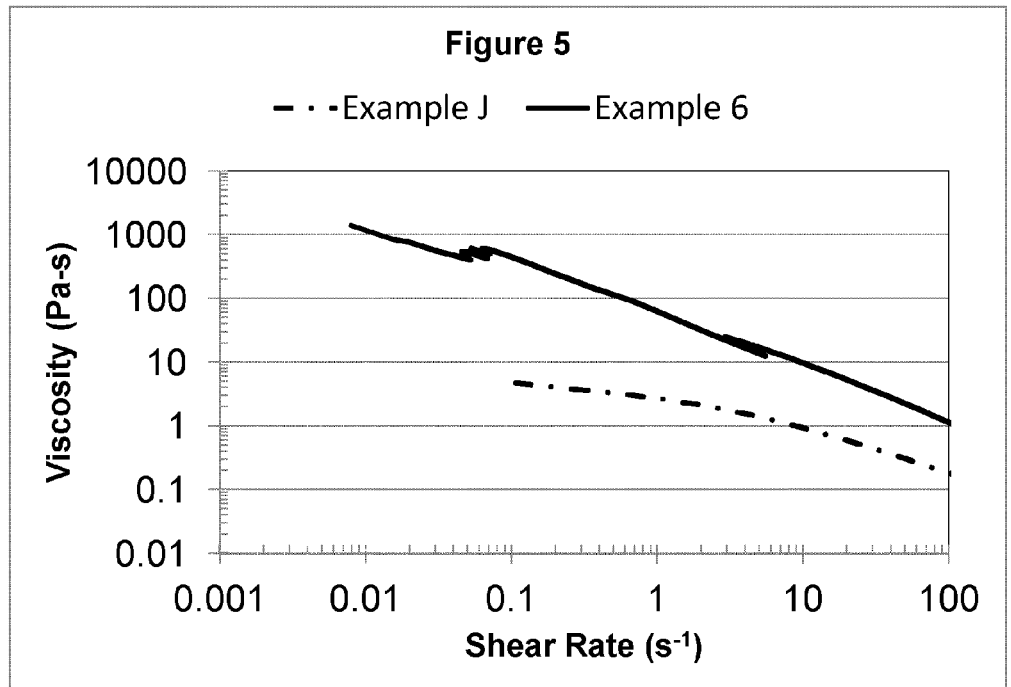
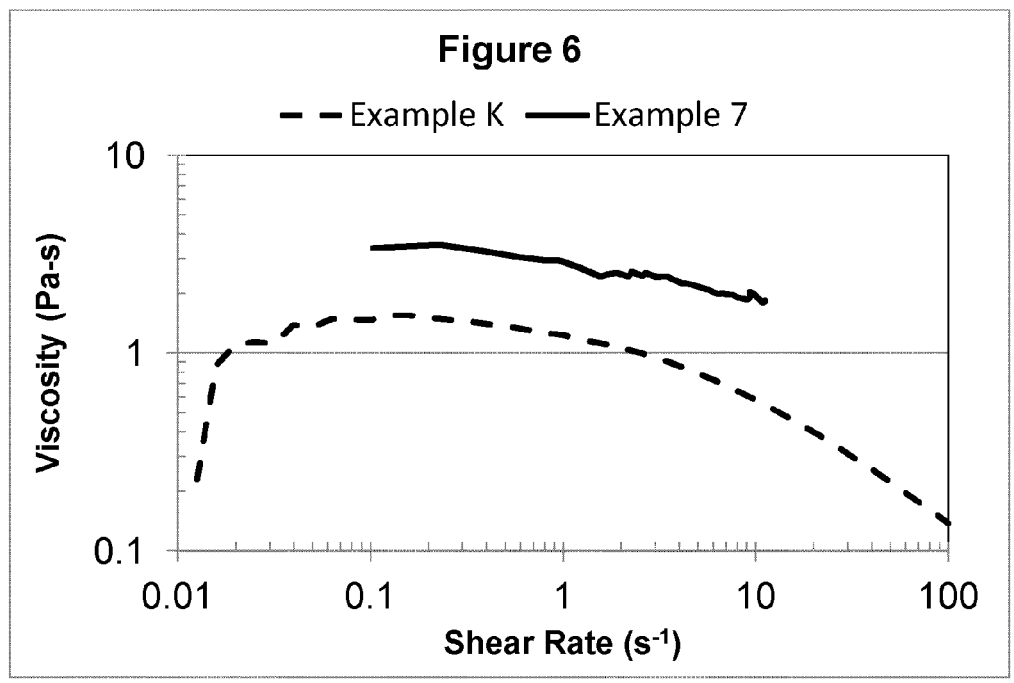

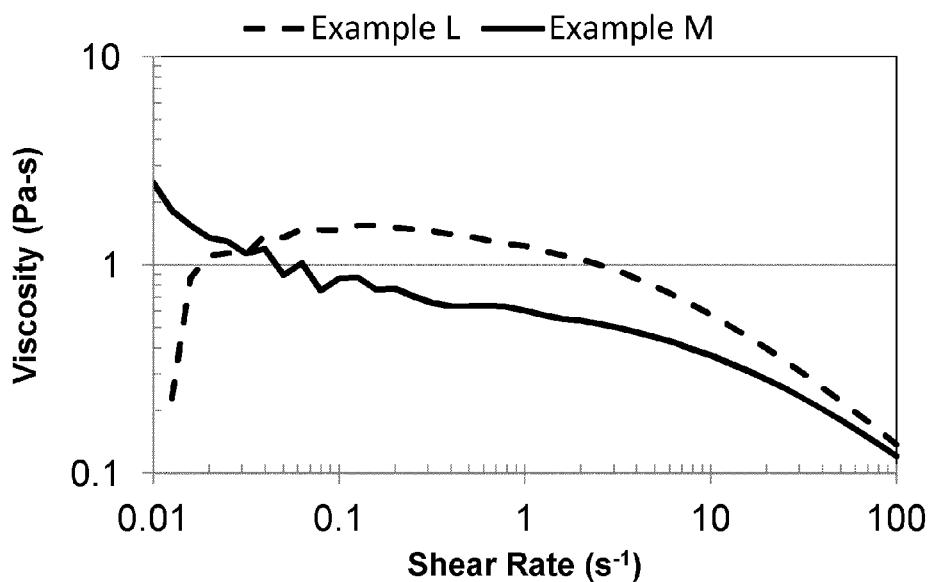
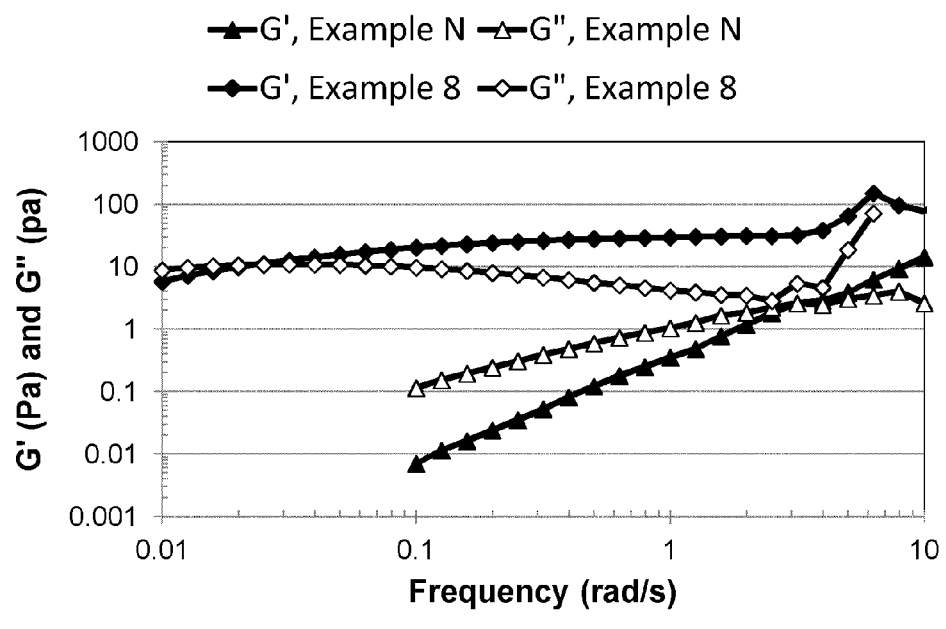

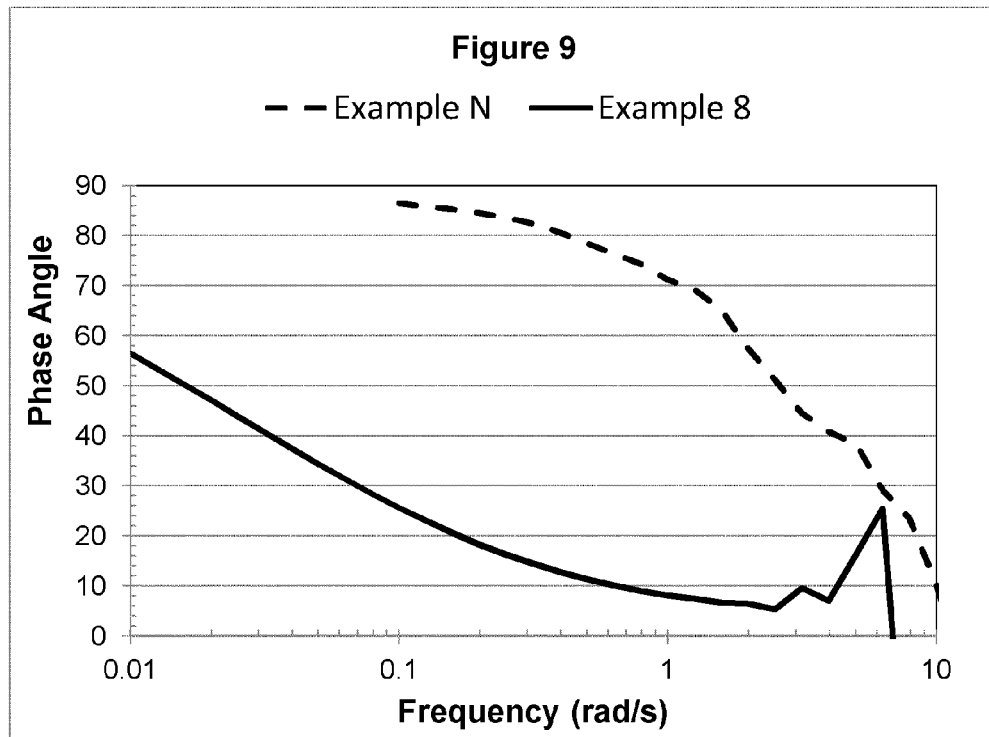
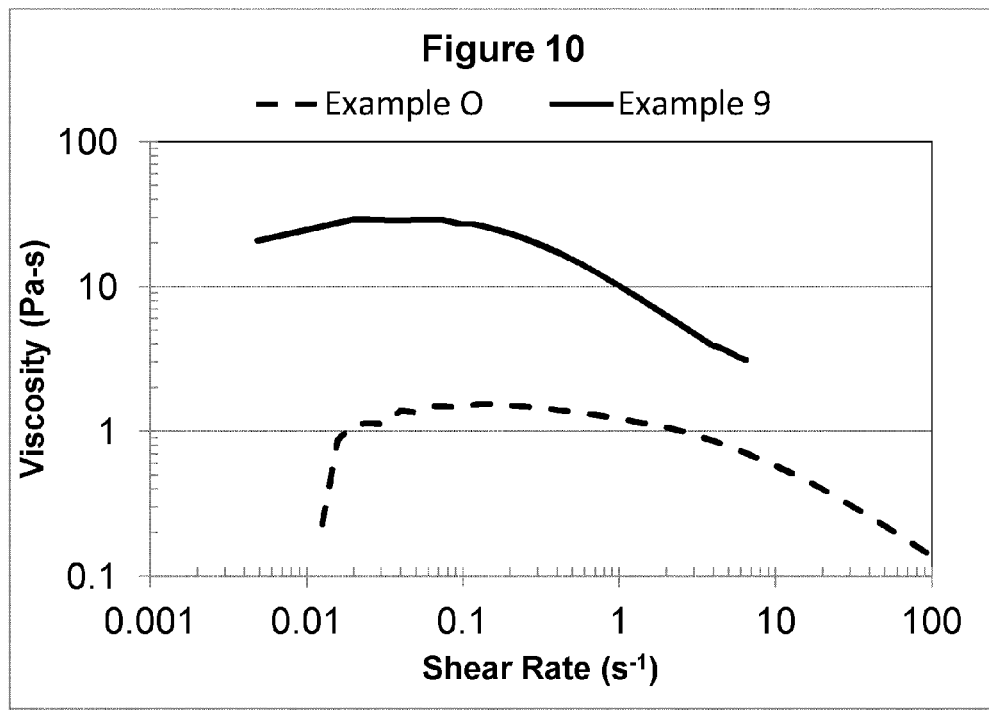

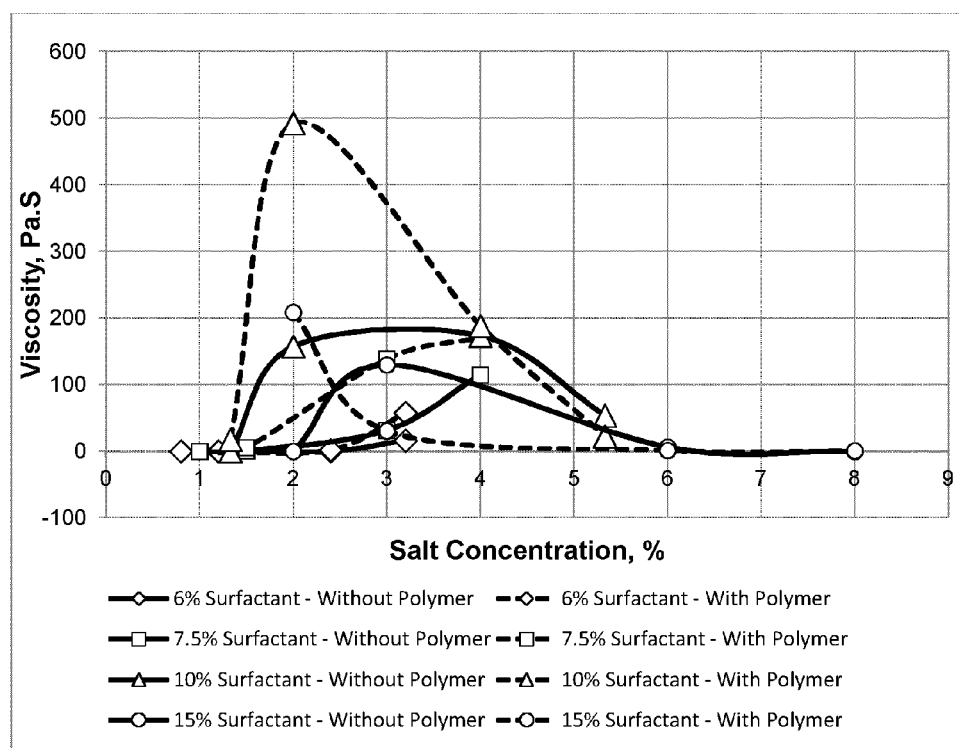

COMPOSITIONS OF VISCOELASTIC SURFACTANT AND HYDROPHOBICALLY MODIFIED POLYMER AS AQUEOUS THICKENERS

This application is a National Stage entry of International Application PCT/EP2011/072861, filed Dec. 15, 2011, which claims the benefit of U.S. Patent Application No. 61/423,710, filed Dec. 16, 2010, and European Patent Application No. 11161261.0, filed Apr. 6, 2011. The contents of the aforementioned applications are incorporated herein by reference in their entireties.

FIELD OF THE INVENTION

The present invention relates to an aqueous viscoelastic composition comprising at least one viscoelastic surfactant, and at least one hydrophobically modified polymer, and to the use of such viscoelastic compositions.

BACKGROUND OF THE INVENTION

For various applications it is desired to use liquid compositions with viscoelastic properties. Such compositions, for instance, may be used to stimulate oil wells wherein impeded flow paths lead to an insufficient hydrocarbon production, a technique known as (hydraulic) fracturing, and the specialized fluids used in said technique are referred to as fracturing fluids. For such a fracturing process, the compositions are typically injected via the wellbore into the formation at sufficient pressures to create fractures in the formation rocks, thus creating channels through which the hydrocarbons may more readily flow into the wellbore.

Ideally, fracturing fluids should impart a minimal pressure drop in the pipe within the wellbore during placement and have an adequate viscosity to carry proppant material that prevents the fracture from closing. Moreover, said fracturing fluids should have a minimal leak-off rate to avoid fluid migration into the formation rocks so that, notably, the fracture can be created and propagated. Said fracturing fluid should also degrade so as not to leave residual material that may prevent hydrocarbons to flow into the wellbore.

Early fracturing fluids were constituted of viscous or gelled oil but, more recently, aqueous fracturing fluids mainly comprising linear and/or crosslinked polymeric gels such as guar, guar derivatives or hydroxyethyl cellulose were introduced. Also, polymer-free aqueous fracturing fluids based on viscoelastic surfactants were developed. The principal advantages of viscoelastic surfactant fluids are ease of preparation, minimal formation damage and high retained permeability in the proppant pack, being the conventional proppant additives in the fracturing fluids. Many viscoelastic fluids, including aqueous fracturing fluids, are known comprising a viscoelastic surfactant. According to a conventional theory, the viscoelastic surfactant molecules, present at a sufficient concentration, aggregate into overlapping worm- or rod-like micelles, which confer the necessary viscosity to the fluid to carry the proppant during fracturing. In addition, viscoelastic surfactant based fluids are "responsive" in that they degrade to low viscosity fluid by contacting and interacting with formation fluids, in particular hydrocarbons, during backflow from the reservoir to the wellbore.

It is noted that WO 2003/056130 proposes an improvement on such existing systems and proposes to use a combination of viscoelastic surfactants and a hydrophobically modified polymer, wherein the concentration of the hydrophobically modified polymer is comprised between its overlap concentration $c^*$ and its entanglement concentration $c_e$. Although the viscoelastic fluids of WO 2003/056130 have certain commercial value, they contain high amounts of both surfactant and hydrophobically modified polymer in order to achieve aqueous compositions with the desired viscosity. Further, in the polymer, the hydrophobes are connected to the polymer backbone via a degradable group.

It is noted that also in U.S. Pat. No. 4,432,881 liquids are used wherein a water-soluble polymer with hydrophobic groups is used. The polymers that are taught to be used have a weight average molecular weight of 200,000 to 5 million Dalton.

The high molecular weight polymers are difficult to dissolve and difficult to distribute homogeneously in aqueous formulations. They also tend to leave residues on rock formation and cause damage of the formation.

There is a need in the art for aqueous viscoelastic surfactant based fluids with a further reduced amount of chemicals to obtain a certain viscosity or compositions with a higher viscosity when the same amount of chemicals is used, the amounts being based on the weight of the chemicals in the final composition, thereby further reducing the costs involved in the use of said fluid and/or expanding the applications wherein the compositions can be used. Also there is a need to be able to use polymers that are more easily dispersible in aqueous formulations.

SUMMARY OF THE INVENTION

It is an object of the present invention to at least meet the above mentioned needs in the art.

Surprisingly, the present inventors have found that viscoelastic compositions can be produced that do not suffer from the drawbacks of the compositions of the prior art when using one or more specific viscoelastic surfactants and one or more specific hydrophobically modified polymers.

In a first aspect, the present invention thus provides an aqueous viscoelastic composition comprising
  a. at least one viscoelastic surfactant, and
  b. at least one hydrophobically modified polymer, which:
    i. is formed from polymerization of ethylenically unsaturated monomers;
    ii. has a number average molecular weight (Mn) of from 1,000 to 100,000 Dalton (Da); and
    iii. for at least 0.1 mole %, based on the amount of monomer units in the polymer, comprises monomeric units each covalently bonded to a straight, branched or cyclic, saturated or unsaturated pendant, optionally alkoxylated, hydrocarbyl group having from 6 to 40 carbon atoms, said pendant, optionally alkoxylated, hydrocarbyl group being connected to the backbone of said hydrophobically modified polymer via a non-ester containing linking group.

In a second aspect, the present invention relates to the use of the hydrophobically modified polymer, as described herein, as a thickener for a viscoelastic composition comprising a viscoelastic surfactant.

In a third aspect, the present invention relates to different uses of an aqueous viscoelastic composition of the present invention, such as a fracturing fluid for the fracturing of rock formations and as thickener in different applications.

In a fourth aspect, the present invention relates to a method for fracturing of a rock formation, utilizing an aqueous viscoelastic fluid of the present invention as the fracturing fluid.

These and other aspects of the present invention will now be described more in detail.

BRIEF DESCRIPTION OF THE DRAWINGS

The FIGS. 1-11 shows plotted results of various experiments as is described herein.

DETAILED DESCRIPTION

The present invention concerns aqueous viscoelastic fluids, preferably aqueous fracturing fluids for, inter alia, use in the recovery of hydrocarbons such as oil and gas. The viscoelastic fluid of the invention comprises a special combination of one or more viscoelastic surfactants and one or more specific hydrophobically modified polymers.

The property of viscoelasticity in general is well known and reference is made to Hoffmann et al., "Influence of Ionic Surfactants on the Viscoelastic Properties of Zwitterionic Surfactant Solutions", *Langmuir*, 8, 2140-2146, (1992).

Herein the test method for viscoelasticity is to apply sinusoidal shear deformation to the composition and to measure the storage shear modulus (G') and the loss shear modulus (G") at a given temperature. If the elastic component (storage shear modulus G') is at least as large as the viscous component (loss shear modulus G"), that is G'≥G", at some point or over some range of points below a frequency of about 10 rad/sec, typically between about 0.001 to about 10 rad/sec, more typically between 0.1 to 10 rad/sec, at a given temperature and if G'>$10^{-2}$ Pascal, preferably more than $10^{-1}$ Pascal, the fluid is considered viscoelastic at that temperature. The definition and the rheological measurement of G' and G" are generally described in Barnes H. A. et al., *An Introduction to Rheology*, pp. 45-54, Elsevier, Amsterdam (1997).

The viscoelastic surfactant is of the conventional type and can inter alia be selected from amine oxide surfactants including amidoamine oxide surfactants, amphoteric surfactants, zwitterionic surfactants, anionic surfactants, cationic surfactants and mixtures of two or more thereof.

It is well known that viscoelastic surfactants provide viscoelasticity by forming a different type of micelle than the usual spherical micelles formed by most surfactants. Viscoelastic surfactants form elongated, often cylindrical, micelles which can be described as worm-like, thread-like, or rod-like micelles. In the context of the present invention, a viscoelastic surfactant is thus a surfactant which can form micelles in a fluid, which micelles imparts viscoelasticity to the fluid. Usually, it is said that the shape and size of a micelle is a function of the molecular geometry of its surfactant molecules and solution conditions such as surfactant concentration, temperature, pH, and ionic strength. The formation of long, cylindrical micelles creates useful rheological properties. Viscoelastic surfactant exhibits shear-thinning behavior, and remains stable despite repeated high shear applications, as disrupted micelles reform spontaneously when the shear is lowered. By comparison, a typical polymeric thickener will irreversibly degrade when subjected to high shear applications.

Amine oxide surfactants contemplated for use as viscoelastic surfactants in the present invention include those of the following structural formula (I):

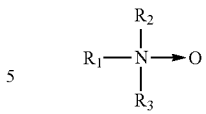
(I)

where $R_1$ is a hydrophobic moiety of alkyl, alkenyl, cycloalkyl, alkylarylalkyl, alkoxyalkyl, alkylaminoalkyl or alkylamidoalkyl. $R_1$ has from about 8 to about 30 carbon atoms and may be straight- or branched-chained and saturated or unsaturated. Examples of long chain alkyl groups include, but are not limited to, octadecenyl (oleyl), octadecyl (stearyl), docosenoic (erucyl), and the derivatives of tallow, coco, soy, and rapeseed oils.

$R_2$ and $R_3$ are, independently, hydrogen or at least partially aliphatic groups having from 1 to about 30 carbon atoms, preferably from about 1 to about 20 carbon atoms, more preferably from about 1 to about 10 carbon atoms, and most preferably from about 1 to about 6 carbon atoms. Representative at least partially aliphatic groups include alkyl, alkenyl, cycloalkyl, alkylaryl, hydroxyalkyl, carboxyalkyl, and hydroxyalkyl-polyoxyalkylene. The aliphatic group can be straight- or branched-chained and saturated or unsaturated.

Amidoamine oxide surfactants contemplated for use as viscoelastic surfactants in the present invention include those of the following structural formula (II):

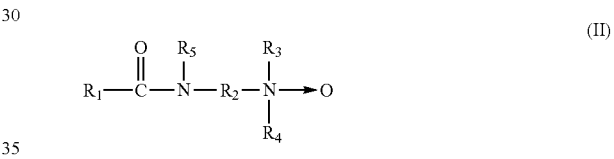
(II)

where $R_1$ is a straight- or branched-chained and saturated or unsaturated aliphatic group of from about 8 to about 30 carbon atoms, preferably from about 14 to about 21 carbon atoms. More preferably, $R_1$ is a fatty aliphatic derived from natural fats and oils having an iodine value of from about 1 to about 140, preferably from about 30 to about 90, and more preferably from 40 to about 70. $R_1$ may be restricted to a single chain length or may be of mixed chain length, such as those groups derived from natural fats and oils or petroleum stocks. Preferred are tallow alkyl, hardened tallow alkyl, rapeseed alkyl, hardened rapeseed alkyl, tall oil alkyl, hardened tall oil alkyl, coco alkyl, oleyl, or soya alkyl;

$R_2$ is a straight- or branched-chained, substituted or unsubstituted, divalent alkylene group of from 2 to about 6 carbon atoms, preferably of from 2 to 4 carbon atoms, and more preferably of 3 carbon atoms;

$R_3$ and $R_4$ are the same or different and are selected from alkyl or hydroxyalkyl groups of from 1 to about 4 carbon atoms and are preferably hydroxyethyl or methyl. Alternatively, $R_3$ and $R_4$ in the amidoamine oxide of formula (II) together with the nitrogen atom to which these groups are bonded form a heterocyclic ring of up to 6 members; and $R_5$ is hydrogen or a $C_1$-$C_4$ alkyl or hydroxyalkyl group.

Examples of amidoamine oxide contemplated by the present invention include but are not limited to those selected from the group consisting of tallow amidoalkylamine oxide, hardened tallow amidoalkylamine oxide, rapeseed amidoalkylamine oxide, hardened rapeseed amidoalkylamine oxide, tall oil amidoalkylamine oxide, hardened amidoalkylamine oxide, coco amidoalkylamine oxide, stearyl amidoalkylamine oxide, oleyl amidoalkylamine oxide, soya amidoalkylamine oxide, and mixtures thereof. Preferred specific examples of the amidoamine oxides of the present invention include but are not limited to the following: tallow amidopropyl dimethylamine oxide, hydrogenated tallow amidopropyl dimethylamine oxide, soya amidopropyl dimethylamine oxide, oleyl amidopropyl dimethylamine oxide, erucyl amidopropyl dimethylamine oxide, rapeseed amidopropyl dimethylamine oxide, hydrogenated rapeseed amidopropyl dimethylamine oxide, tall oil amidopropyl dimethylamine oxide, hydrogenated tall oil amidopropyl dimethylamine oxide, C14-C22 saturated or unsaturated fatty acid amidopropyl dimethylamine oxides, and mixtures thereof.

A cationic surfactant has a positively charged moiety regardless of pH. Cationic surfactants contemplated for use as viscoelastic surfactant in the present invention include those selected from quaternary salts, certain amines, and combinations thereof. The quaternary salts have the structural formula (III)

where $R_1$ is a hydrophobic moiety of alkyl, alkenyl, cycloalkyl, alkylarylalkyl, alkoxyalkyl, alkylaminoalkyl or alkylamidoalkyl. $R_1$ has from about 8 to about 30 carbon atoms and may be straight- or branched-chained and saturated or unsaturated. Examples of long chain alkyl groups include, but are not limited to, octadecenyl (oleyl), octadecyl (stearyl), docosenoic (erucyl), and the derivatives of tallow, coco, soy, and rapeseed oils;

$R_2$, $R_3$ and $R_4$ are, independently, at least partially aliphatic groups having from 1 to about 30 carbon atoms, preferably from about 1 to about 20 carbon atoms, more preferably from about 1 to about 10 carbon atoms, and most preferably from about 1 to about 6 carbon atoms. Representative at least partially aliphatic groups include alkyl, alkenyl, alkylaryl, alkoxyalkyl, hydroxyalkyl, carboxyalkyl, and hydroxyalkylpolyoxyalkylene. The aliphatic group can be straight- or branched-chained and saturated or unsaturated, and;

$X^-$ is a suitable counter-anion. The counter-anion is typically an inorganic anion such as a sulfate such as $(CH_3)_2SO_4^-$, a nitrate, a perchlorate or a halide such as $Cl^-$, $Br^-$, or an aromatic organic anion such as salicylate, naphthalene sulfonate, p- and m-chlorobenzoates, 3,5-, 3,4-, and 2,4-dichlorobenzoates, t-butyl and ethyl phenate, 2,6- and 2,5-dichlorophenates, 2,4,5-trichlorophenate, 2,3,5,6-tetrachlorophenate, p-methyl phenate, m-chlorophenate, 3,5,6-trichloropicolinate, 4-amino-3,5,6-trichloropicolinate, 2,4-dichlorophenoxyacetate.

The amines have the following structural formula (IV):

where $R_1$, $R_2$, and $R_3$ have the meaning as defined above for the quaternary salt residues $R_1$, $R_2$, and $R_3$, respectively.

The zwitterionic surfactant has a permanently positively charged moiety in the molecule regardless of pH and a negatively charged moiety at alkaline pH. Zwitterionic surfactants that are useful as viscoelastic surfactants in the present invention include those of the following structural formula (V):

where $R_1$ is a hydrophobic moiety of alkyl, alkenyl, cycloalkyl, alkylarylalkyl, alkoxyalkyl, alkylaminoalkyl or alkylamidoalkyl. $R_1$ has from about 8 to about 30 carbon atoms and may be straight- or branched-chained and saturated or unsaturated. Examples of long chain alkyl groups include, but are not limited to, octadecenyl (oleyl), octadecyl (stearyl), docosenoic (erucyl), and the derivatives of tallow, coco, soy, and rapeseed oils;

$R_2$ and $R_3$ are, independently, at least partially aliphatic groups having from 1 to about 30 carbon atoms, preferably from about 1 to about 20 carbon atoms, more preferably from about 1 to about 10 carbon atoms, and most preferably from about 1 to about 6 carbon atoms. Representative at least partially aliphatic groups include alkyl, alkenyl, alkylaryl, alkoxyalkyl, hydroxyalkyl, carboxyalkyl, and hydroxyalkylpolyoxyalkylene.

The aliphatic group can be straight- or branchedchained and saturated or unsaturated, and;

$R_4$ is a hydrocarbyl radical (e.g. alkylene) with a chain length of 1 to 4 carbon atoms. Preferred are methylene or ethylene groups.

When it is zwitterionic, the surfactant is associated with both negative and positive counter-ions. Anions are typically as defined above for $X^-$ for the cationic surfactant. In one embodiment any cation is suitably selected from $Na^+$, $K^+$, $NH_4^+$, and amine salts, such as $(CH_3)_2NH_2^+$.

An amphoteric surfactant has both a positively charged moiety and a negatively charged moiety over a certain pH range (e.g. typically slightly acidic), only a negatively charged moiety over a certain pH range (e.g. typically slightly alkaline), and only a positively charged moiety at a different pH (e.g. typically moderately acidic).

Amphoteric surfactants contemplated for use as viscoelastic surfactant in the present invention include those represented by the following structural formula (VI):

where $R_1$ is a hydrophobic moiety of alkyl, alkenyl, cycloalkyl, alkylarylalkyl, alkoxyalkyl, alkylaminoalkyl or alkylamidoalkyl. $R_1$ has from about 8 to about 30 carbon atoms and may be straight- or branched-chained and saturated or unsaturated. Examples of long chain alkyl groups include, but are not limited to, octadecenyl (oleyl), octadecyl (stearyl), docosenoic (erucyl), and the derivatives of tallow, coco, soy, and rapeseed oils;

$R_2$ has the meaning as defined above for the residue $R_2$ of the zwitterionic surfactant;

$R_3$ is a hydrocarbyl radical (e.g. alkylene) with a chain length of 1 to 4 carbon atoms. Preferred are methylene or ethylene groups.

An anionic surfactant has a negatively charged moiety regardless of pH. Anionic surfactants contemplated for use as the viscoelastic surfactant in the present invention include those of the following structural formulae (VII) and (VIII).

R—Z (VII)

R—X—Y—Z (VIII)

where R is the hydrophobic moiety of alkyl, alkenyl, cycloalkyl, alkylarylalkyl, alkoxyalkyl, alkylaminoalkyl or alkylamidoalkyl. Preferably, R is a saturated or unsaturated, straight or branched alkyl chain of from 8 to 30 carbon atoms. Examples of long alkyl chain groups include, but are not limited to, octadecenyl (oleyl), lauryl, octadecyl (stearyl), docosenoic (erucyl), and the derivatives of tallow, coco, soy, and rapeseed oils.

Z is the negatively charged hydrophilic head of the surfactant. Z is suitably selected from the group consisting of carboxylate $COO^-$, sulfonate $SO_3^-$, sulfate $SO_4^-$ phosphonate, phosphate, and combinations thereof. In one embodiment Z is a carboxylate group $COO^-$ or a sulfonate group $SO_3^-$ or a sulfate group $SO_4^-$.

X is a stabilizing group. X is preferably a cleavable bond. Preferably, X is an ester, amide, reverse ester or reverse amide group.

Y is a space group which separates the cleavable group X and the hydrophilic head of the surfactant. Y is preferably a linear, saturated or unsaturated hydrocarbon chain of 1, 2 or 3 carbon atoms or a branched, saturated or unsaturated hydrocarbon chain where the main chain is of 1, 2 or 3 carbon atoms, possibly incorporating an aromatic ring.

The surfactant of the invention may be dimeric or oligomeric. In such case, the formula of the surfactant is $[R-Z]_n$ or $[R-X-Y-Z]_n$, where n is 2-10, preferably 2 or 3. An example of an oligomeric anionic surfactant is oligomerized oleic acid, which generally leads to complex mixtures of dimeric and trimeric products. Commercially available oligomers, such as the Empol™ series of dimmers and trimers, are suitable for use in accordance with the present invention.

When the surfactant is anionic, the counter-ion is typically $Na^+$, $K^+$, $NH_4^+$, or amine salt such as $(CH_3)_2NH_2^+$. These mono-, di- or oligomeric carboxylates or sulfonates form viscoelastic aqueous compositions in the presence of salt.

Preferably the surfactants that are used are biodegrable, more preferably readily biodegradable, when testing using conventional tests such as OECD 306 A-F.

The hydrophobically modified polymers can be anionic hydrophobically modified polymer or cationic hydrophobically modified polymer or non-ionic hydrophobically modified polymer or zwitterionic hydrophobically modified polymer.

The at least one hydrophobically modified polymer is formed from polymerization of ethylenically unsaturated monomers using polymerization conditions known to those skilled in the art.

The hydrophobically modified polymer has a number average molecular weight of from 1,000, such as from 1,500, for example from 2,500, to 100,000, such as to 90,000, for example to 50,000, such as to 25,000 Da. In the context of this invention, the weight average and number average polymer molecular weights are as determined with size exclusion chromatography. The size exclusion chromatography was performed using HPLC grade water comprising 0.025M $NaH_2PO_4$, 0.025 M $Na_2HPO_4$, and 0.01M of sodium azide which was filtered through a 0.2 µm filter as the eluent and four separation columns, G6000PWxI 7.8 mm×30 cm, G4000PWxI 7.8 mm×30 cm, G3000PWxI 7.8 mm×30 cm, and TSKgel Guard PWxI 6.0 mm×4 cm as the G2500 Guard column (all ex Tosoh Bioscience). Polyacrylic acid sodium salt standards (ex American Polymer Standards Corporation) were used for calibration. The polymers are prepared in water at a concentration of 0.1% w/w. The weight average (Mw) and number average molecular weight (Mn) of the standards are:

| 1. | Mw | 1,300 Dalton | Mn | 830 Dalton |
| 2. | Mw | 8,300 Dalton | Mn | 6200 Dalton |
| 3. | Mw | 83,400 Dalton | Mn | 47,900 Dalton |
| 4. | Mw | 495,000 Dalton | Mn | 311,300 Dalton |
| 5. | Mw | 1,700,000 Dalton | Mn | 1,100,000 Dalton |

Injection column was 450 µL for the standard and sample. Inject the standards and build a first-order or second-order calibration curve. Choose the curve with the best fit and within the range of the sample molecular weight. Run time was 60 minutes per injection for standard and sample.

To a level of at least 0.1 mole %, based on the amount of monomer units in the polymer, the hydrophobically modified polymer comprises monomeric units each covalently bonded to a pendant, optionally alkoxylated, hydrocarbyl group having from 6 to 40 carbon atoms, said pendant, optionally alkoxylated, hydrocarbyl group being connected to the backbone of said hydrophobically modified polymer via a non-ester containing linking group.

The pendant, optionally alkoxylated, hydrocarbyl group has from 6, preferably from 8, more preferably from 11, for example from 14, to 40, preferably to 32, more preferred to 24 carbon atoms.

The pendant hydrocarbyl group is typically a straight, branched or cyclic, saturated or unsaturated hydrocarbyl, such as a linear or branched alkyl, alkenyl, cycloalkyl, aryl, alkylaryl, alkenylaryl or an alkoxylated derivative thereof. The hydrocarbyl group can optionally be alkoxylated, such as obtained by ethoxylating, propoxylating and/or butoxylating the alcohol or acid corresponding to the hydrocarbyl group. If alkoxylated, the alkyleneoxy group(s) will be located between the hydrocarbyl group and the polymer backbone. Examples of pendant hydrocarbyl groups include behenyl, stearyl, lauryl, 2-etylhexyl, 2-propylheptyl, 2-butyloctyl, 2-hexyldecyl, 2-octyldodecyl, 2-decyltetradecyl, 2-dodecylhexadecyl, 2-tetradecyloctadecyl or their alkoxylated derivatives, or the alkyl group of oleyl, coco, soya, erucyl or tallow acids or alcohols or amines and their alkoxylated derivatives. When the hydrocarbyl is alkoxylated, the carbon atoms in the alkyleneoxy-groups are included in the carbon atom count of the hydrocarbyl group, except for the carbon atoms of any ethyleneoxy-groups, which are not included in the carbon atom count of the hydrocarbyl group due to the hydrophilicity of the ethyleneoxy-group. To illustrate, an ethoxylated dodecyl group is an alkoxylated hydrocarbyl group having 12 carbon atoms, whereas hexyl propoxylated with 3 propoxylenoxy groups is an alkoxylated hydrocarbyl group having 15 (6+9) carbon atoms.

In one embodiment of the invention the pendant, optionally alkoxylated, hydrocarbyl group contains 12 or more carbons and the hydrophobically modified polymer contains, to a level of from 0.1, such as from such as from 0.5, for example from 1, to 20, such as to 10, for example to 5 mole %, based on the amount of monomer units in the polymer, monomeric units connected to such pendant, optionally alkoxylated, hydrocarbyl group.

In another embodiment of the invention the pendant, optionally alkoxylated hydrocarbyl group comprises an alkyl function with at most 11 carbon atoms and the, hydrophobically modified polymer contains, to a level of from 0.1, such as from such as from 0.5, for example from 1, to 20, such as to 10, for example to 5 mole %, based on the amount of monomer units in the polymer, monomeric units connected to such pendant, optionally alkoxylated, hydrocarbyl group.

The pendant, optionally alkoxylated, hydrocarbyl group is connected to the backbone of the hydrophobically modified polymer by via a non-ester containing linking group, such as a direct bond or urea, urethane, imide or amide containing linking groups. Exemplary non-ester containing linking groups include a direct bond or:

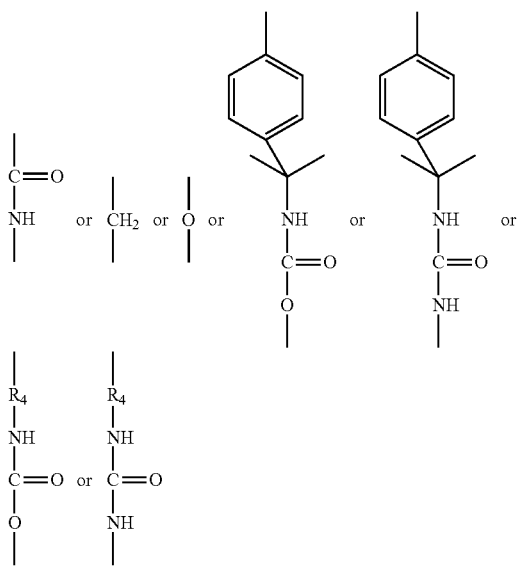

wherein $R_4$ is a hydrocarbylene group having 1 to 10 carbon atoms, preferably $CH_2$, and the top bond of the linking group is connected to the polymer backbone and the bottom bond is connected to the pendant, optionally alkoxylated, hydrocarbyl group. Preferably, the non-ester containing linking group is a direct bond or a urea, urethane, imide or amide containing linking group, more preferably a urea or urethane containing linking group.

The hydrophobically modified polymers used in the invention can be produced by copolymerizing suitable ethylenically unsaturated monomers to directly achieve the desired polymer, or they can also be produced by modification of an existing polymer, by reacting a hydrophobically modified polymer with further hydrophobic modification agents, such as such as reacting a copolymer of maleic anhydride, including polyisobutylene succinic acid copolymers (PIBSA), with a fatty amine.

Alternatively, the hydrophobically modified polymer may be produced by reacting a functional polymer with a hydrophobic modification agent.

The hydrophobically modified polymer is suitably free from, or contains at most 1, preferably at most 0.1, more preferably at most 0.01 mole %, based on the amount of monomer units in the polymer, of monomeric units connected to pendant, optionally alkoxylated, hydrocarbyl group having at least 10, preferably at least 8, more preferably at least 6 carbon atoms connected to the backbone of said hydrophobically modified polymer via an ester containing linking group.

The hydrophobically modified polymer may be obtained by copolymerizing at least a first and at least a second ethylenically unsaturated monomer, wherein said first monomer is an ethylenically unsaturated monomer with an optionally-alkoxylated hydrocarbyl group having from 6, preferably from 8, more preferably from 11, to 40, preferably to 32, more preferably to 24 carbon atoms being connected to the unsaturated function of said monomer via a non-ester containing linking group, preferably a direct bond or a urea, urethane, imide or amide containing linking group, more preferably a urea or urethane containing linking group; and said second monomer is an ethylenically unsaturated monomer free from hydrocarbyl groups having at least 11, preferably at least 8, more preferably at least 6 carbon atoms connected to the unsaturated function of the monomer. The first and second monomers are present in a molar ratio of from 0.1:99.9 to 90:10.

When the optionally-alkoxylated hydrocarbyl group has at least 12 carbon atoms, the first and second monomers are usually present in a molar ratio of from 0.1:99.9 to 20:80; preferably from 0.5:99.5 to 10:90, more preferably from 1:99 to 5:95.

When the optionally-alkoxylated hydrocarbyl group has at most 11 carbon atoms, the first and second monomers are usually present in a mutual molar ratio of from 1:99 to 90:10; preferably from 5:95 to 70:30, more preferably from 10:90 to 50:50.

Monomers with an optionally-alkoxylated hydrocarbyl group having from 6 to 40 carbon atoms connected to the unsaturated function thereof via a non-ester containing linking group (herein also referred to hydrophobe-bearing monomers) include those with the following structure (VIII)

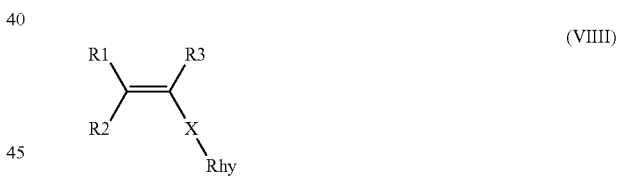

where
R1, R2, and R3 are independently selected from H, $CH_3$, COOH, and $CH_2COOH$,
X (i.e. the linking group) is a direct bond or

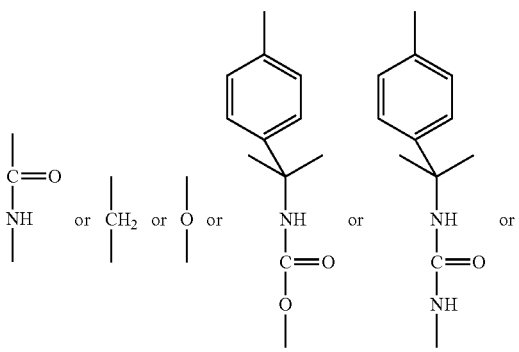

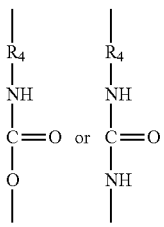

wherein R4 is a hydrocarbylene group having from 1 to 10 carbon atoms, preferably CH$_2$, the top bond of X is connected to the double bond in (VIII) and the bottom bond of X is connected to Rhy, and Rhy is the optionally-alkoxylated hydrocarbyl group having from 6, preferably from 8, more preferably from 11, to 40, preferably to 32, more preferably to 24 carbon atoms.

Hydrophobe-bearing monomers of the above type are commercially available or can be obtained by methods well known in the art, for example by reacting a ethylenically unsaturated isocyanate, such as allyl-isocyanate or 3-isopropyl-benzyl-α,α-dimethyl-isocyanate, with an alcohol or amine containing a hydrocarbyl group (optionally alkoxylated) having from 6 to 40 carbon atoms, by reacting an ethylenically unsaturated acid monomer, such as acrylic acid, with an amine containing a hydrocarbyl group (optionally alkoxylated) having from 6 to 40 carbon atoms. Other methods to synthesize such monomers are well known to the person skilled in the art of organic synthesis. Examples of hydrophobe-bearing monomers where the hydrophobe is linked to the double bond of the monomer include t-octyl acrylamide, n-octyl acrylamide, lauryl acrylamide, stearyl acrylamide, behenyl acrylamide, 1-allyl naphthalene, 2-allyl naphthalene, 1-vinyl naphthalene, 2-vinyl naphthalene, styrene, α-methyl styrene, 3-methyl styrene, 4-propyl styrene, t-butyl styrene, 4-cyclohexyl styrene, 4-dodecyl styrene, 2-ethyl-4-benzyl styrene and 4-(phenyl butyl) styrene.

The ethylenically unsaturated monomer free from hydrocarbyl groups having 11 or more, preferably 8 or more, more preferably 6 or more, carbon atoms connected to the unsaturated function of the monomer, i.e. the second monomer, may be anionic ethylenically unsaturated monomers, cationic ethylenically unsaturated monomers, non-ionically ethylenically unsaturated monomers, zwitterionic ethylenically unsaturated monomers, mixtures thereof and salts thereof.

In one embodiment, the hydrophobically modified polymer is anionic and is synthesized from at least one first ethylenically unsaturated hydrophobe-bearing monomer and at least one second ethylenically unsaturated monomer that is anionic and referred to as an anionic ethylenically unsaturated monomer here forth. In another embodiment, the hydrophobically modified polymer is cationic and is synthesized from at least one first ethylenically unsaturated hydrophobe-bearing monomer and at least one second ethylenically unsaturated monomer that is cationic and is referred to as a cationic ethylenically unsaturated monomer here forth. In yet another embodiment, the hydrophobically modified polymer is non-ionic and is synthesized from at least one first ethylenically unsaturated hydrophobe-bearing monomer and at least one second ethylenically unsaturated monomer that is non-ionic and is referred to as a non-ionic ethylenically unsaturated monomer here forth. In a further embodiment, the hydrophobically modified polymer is zwitterionic and is synthesized from at least one first ethylenically unsaturated hydrophobe-bearing monomer and at least one second ethylenically unsaturated monomer that is zwitterionic and is referred to as a zwitterionic ethylenically unsaturated monomer here forth. In this embodiment, the polymer contains positive and negative charges which are on the same monomer repeat unit. In yet another embodiment, the hydrophobically modified polymer is zwitterionic and is synthesized from at least one first ethylenically unsaturated hydrophobe-bearing monomer and at least one anionic ethylenically unsaturated second monomer and at least one cationic ethylenically unsaturated second monomer. In this embodiment, the polymer contains positive and negative charges which are on different monomer repeat units.

Herein an anionic ethylenically unsaturated monomer is defined as any monomer that is capable of introducing a negative charge to the hydrophobically modified polymer. These anionic ethylenically unsaturated monomers include of acrylic acid, methacrylic acid, ethacrylic acid, α-chloroacrylic acid, α-cyano acrylic acid, β-methyl-acrylic acid (crotonic acid), α-phenyl acrylic acid, β-acryloxy propionic acid, sorbic acid, α-chloro sorbic acid, angelic acid, cinnamic acid, p-chloro cinnamic acid, β-styryl acrylic acid (1-carboxy-4-phenyl butadiene-1,3), itaconic acid, maleic acid, citraconic acid, mesaconic acid, glutaconic acid, aconitic acid, fumaric acid, tricarboxy ethylene, 2-acryloxypropionic acid, 2-acrylamido-2-methyl propane sulfonic acid (AMPS), vinyl sulfonic acid, sodium methallyl sulfonate, sulfonated styrene, allyloxybenzene sulfonic acid, and their salts. The preferred salts of hydrophilic acid monomers are sodium, potassium or ammonium salts. Moieties such as maleic anhydride or acrylamide that can be derivatized to an acid-containing group can be used. Combinations of anionic ethylenically unsaturated monomers can also be used. In one aspect the anionic ethylenically unsaturated monomer is acrylic acid, maleic acid, itaconic acid, methacrylic acid, 2-acrylamido-2-methyl propane sulfonic acid, vinyl sulfonic acid, sodium methallyl sulfonate, sulfonated styrene, allyloxybenzene sulfonic acid or mixtures thereof and their salts.

Cationic ethylenically unsaturated monomers are defined herein as ethylenically unsaturated monomers which are capable of introducing a positive charge to the hydrophobically modified copolymer. In one embodiment of the present invention, the cationic ethylenically unsaturated monomer has at least one amine functionality. The cations in the polymer may be obtained by forming amine salts of all or a portion of the amine functionality, and/or by quaternizing all or a portion of the amine functionality to form quaternary ammonium salts. As used herein, the term "amine salt" means that the nitrogen atom of the amine functionality is covalently bonded to from one to three organic groups and from three to one protons, such that there are 4 bonds to the nitrogen and it is associated with an anion. As used herein, the term "quaternary ammonium salt" means that a nitrogen atom of the amine functionality is covalently bonded to four organic groups and is associated with an anion.

Cationic ethylenically unsaturated monomers that can form cations include N,N-dialkylaminoalkyl(meth)acrylate, N-alkylaminoalkyl(meth)acrylate, N,N-dialkylaminoalkyl (meth)acrylamide, and N-alkylaminoalkyl(meth)acrylamide, where the alkyl groups are independently $C_{1-18}$ cyclic compounds such as 1-vinyl imidazole and the like. Aromatic amine-containing monomers such as vinyl pyridine may also be used. Furthermore, monomers such as vinyl formamide, vinyl acetamide, and the like which generate amine moieties on hydrolysis may also be used. Preferably, the cationic ethylenically unsaturated monomer is N,N-dimethylaminoethyl methacrylate, tert-butyl aminoethyl methacrylate, and N,N-dimethylaminopropyl methacrylamide.

Cationic ethylenically unsaturated monomers that may be used include the quarternized derivatives of the above monomers as well as diallyldimethylammonium chloride also known as dimethyldiallylammonium chloride, (meth)acrylamidopropyl trimethylammonium chloride, 2-(meth)acryloyloxy ethyl trimethyl ammonium chloride, 2-(meth)acryloyloxy ethyl trimethyl ammonium methyl sulfate, 2-(meth)acryloyloxy-ethyltrimethyl ammonium chloride, N,N-dimethylaminoethyl(meth)acrylate methyl chloride quaternary, methacryloyloxy ethyl betaine as well as other betaines and sulfobetaines, 2-(meth)acryloyloxy ethyl dimethyl ammonium hydrochloride, 3-(meth)acryloyloxy ethyl dimethyl ammonium hydroacetate, 2-(meth)acryloyloxy ethyl dimethyl cetyl ammonium chloride, 2-(meth)acryloyloxy ethyl diphenyl ammonium chloride, and others.

As used herein, the term "nonionic ethylenically unsaturated monomer" means an ethylenically unsaturated monomer which does not introduce a charge to the hydrophobically modified copolymer. These nonionic ethylenically unsaturated monomers include acrylamide, methacrylamide, N-alkyl(meth)acrylamide, N,N-dialkyl(meth)acrylamide such as N,N-dimethylacrylamide, hydroxyalkyl(meth)acrylates, alkyl(meth)acrylates such as methylacrylate and methylmethacrylate, vinyl acetate, acrylonitrile, vinyl morpholine, vinyl pyrrolidone, vinyl caprolactum, ethoxylated alkyl, alkaryl or aryl monomers such as methoxypolyethylene glycol(meth)acrylate, allyl glycidyl ether, allyl alcohol, glycerol (meth)acrylate, monomers containing silane, silanol, and siloxane functionalities, and others. In one embodiment the non-ionic hydrophobically modified polymer contains vinyl alcohol which is typically generated by hydrolysis of vinyl acetate after the hydrophobically modified polymer has been formed. The nonionic ethylenically unsaturated monomer is preferably water-soluble.

As used herein, the term "zwitterionic ethylenically unsaturated monomer" means an ethylenically unsaturated monomer which introduces both a positive and a negative charge in the same monomer repeat unit of the hydrophobically modified copolymer. The zwitterionic ethylenically unsaturated monomers include amine oxides carboxybetaine, sulfobetaine, and phosphobetaine monomers. Examples of amine oxides include, but are not limited to, vinyl pyridine-N-oxide and tert-butyl-aminoethylmethacrylate-N-oxide. It is understood that the monomer, say N-vinyl pyridine, can be copolymerized and then the pyridine moiety is oxidized to the amine oxide. Examples of carboxybetaine monomers include, but are not limited to, N,N'-dimethyl-N-methacryloyloxyethyl-N-(2-carboxyethyl) ammonium, (2-(2-acrylamido-2-methylpropyldimethylammonio) ethanoate, 6-(2-acrylamido-2-methylpropyl dimethyl-ammonio) hexanoate, 4-(N,N-diallyl-N-methylammonio) butanoate, and others.

Examples of sulfobetaine monomers include, but are not limited to, sulfopropyldimethylammonioethyl methacrylate, sulfoethyldimethylammonioethyl methacrylate, sulfobutyldimethylammonioethyl methacrylate, sulfohydroxy propyl-dimethylammonioethyl methacrylate, sulfopropyldimethyl ammoniopropylacrylamide, sulfopropyldimethylammoniopropylmethacrylamide, sulfohydroxypropyldimethyl-ammoniopropylmethacrylamide, sulfopropyldimethylammonioethyl acrylate, sulfopropyldiethylammonioethoxyethyl methacrylate, 2-vinyl-l-(3-sulfopropyl) pyridinium betaine, 4-vinyl-l-(3-sulfopropyl) pyridinium betaine, 1-vinyl-3-(3sulfopropyl) imidazolium betaine, sulfopropylmethyldiallylammonium betaine, 3-(N, N-diallyl-N-methylammonio) propanesulfonate, and others.

As mentioned before, a zwitterionic hydrophobically modified polymer can be synthesized by copolymerizing an anionic ethylenically unsaturated monomer and a cationic ethylenically unsaturated monomer with a hydrophobe-bearing monomer. Any combination of anionic and cationic monomers may be used. However, the preferred anionic monomer will introduce a sulfonate group to the copolymer.

A polymer of the present invention may comprise further monomers in addition to those mentioned above.

The hydrophobically modified polymers of the invention are not conventional thickeners, due to their low molecular weight. Accordingly, the molecular weight of said polymers, neutralized or not, may for example be chosen such that they do not thicken a 4 wt % KCl solution in water when used at concentrations of 2 wt % in said KCl solution, at a temperature of 25° C. The molecular weight of the polymer may be chosen such that an aqueous solution of 2 wt % of the polymer and 4 wt % of KCl has a viscosity of 100 or less, preferably 50 or less, most preferably 16 mPa*s or less at shear rate of 100 $sec^{-1}$ and a temperature of 25° C. For comparison, a polymer that is conventionally used in fracturing fluids typically gives a viscosity of well over 100 mPa*s when tested this way.

Because of the exceptional properties observed for the compositions of the invention with the viscoelastic surfactant and the specific polymer, it is possible to reduce the amount of surfactant and/or polymer. Accordingly, it may be desired for economic and environmental reasons to use the polymers of the invention at a polymer concentration that is below the overlap concentration $c^*$. Further, it is noted that the polymers of the invention were found to interact with viscoelastic surfactants in such a way that the combined use leads to increased viscosities at high temperature (tested up to 100° C.) and pressures (tested up to 25 bara).

Another embodiment of the invention concerns a method for recovering hydrocarbons from an oil well by using viscoelastic compositions of the invention, preferably by injecting said compositions into formations of rocks in order to fracture said rocks. Preferably, the viscoelastic surfactants, or mixtures of viscoelastic surfactants, of the invention are so selected that they are biodegradable. More preferably, they are selected such that they are readily biodegradable.

Surprisingly such low molecular weight polymers, that in themselves are typically not thickeners, were found to interact with the viscoelastic surfactants in a way that led to an increased viscosity which is much higher than the viscosity of solution of pure viscoelastic surfactant of the same concentration. It was also surprisingly found that the said increased viscosity can be achieved at a polymer concentration that is lower than its overlap concentration $c^*$. For economic en environmental reasons it may be desired to use the polymers of the invention at a polymer concentration that is below the overlap concentration $c^*$.

The polymer overlap concentration $c^*$ is a threshold concentration when polymer coils begin to densely pack in a solvent. In a dilute polymer solution where polymer concentration is below $c^*$, the polymer coils are separated. In a polymer solution where the polymer concentration is above $c^*$, the polymer coils are densely packed. The detailed definition of $c^*$ is described by Pierre-Gilles de Gennes in "Scaling Concept on Polymer Physics", pp. 76-77, Cornell University Press, Ithaca and London (1979). $c^*$ is measured by the plot of viscosity versus concentration. At low concentrations, the plot will follow a linear path and once the $c^*$ is reached, the slope of the line drastically increases. For the purposes herein, the polymer overlap concentration $c^*$ is measured at 25° C. at atmospheric pressure in the solvent.

According to a non-binding theory, the hydrophobically modified polymers of the invention, notably its pendant hydrophobic chains, interact in an improved way with the surfactant micelles. This interaction conceivably increases the worm- or rod-like micelle size, and/or cross-linked the micelles, so that a higher viscosity is achieved. As a result, an aqueous viscoelastic structure that satisfies the required rheology profile is obtained using less amount of chemicals than previously possible. At the same time the lower molecular weight polymers allowed easier handling of the polymer itself and faster preparation of the compositions of the invention.

If the combination of viscoelastic surfactant and polymer of the invention is supplied in a concentrated form, it is preferably in an aqueous, essentially salt-free form. Such an aqueous concentrate has the advantage of having a low viscosity and related easy dilution. Typical aqueous concentrates comprise one or more glycols, such as propyleneglycol, so that the viscoelastic surfactant is more easily dissolved in the concentrate. Typically, the amount of viscoelastic surfactant in such a concentrate is within the range of 10-60% w/w, whereas the amount of polymer ranges from 5-30% w/w, based on the weight of the concentrate. By the term essentially salt-free is meant that the salt concentration is less than 0.01% w/w, otherwise the viscosity becomes unacceptably high.

For aqueous oilfield fracturing fluids, the viscoelastic surfactant is used in an amount of 10% w/w or less. In one embodiment of the invention it is 5% w/w or less. For applications outside oilfield fracturing fluids, the viscoelastic surfactant is used in an amount below 50% w/w, preferentially, below 40% w/w of the final aqueous composition. Also, the viscoelastic surfactant is suitably used in an amount of 0.1% w/w or more. In one embodiment it is 0.2% w/w or more, while in another embodiment it is 0.3% w/w or more, all being based on the weight of the total viscoelastic fluid.

In general, the hydrophobically modified polymer is used in an amount of 10% w/w or less. In one embodiment of the invention it is 5% w/w or less. In another embodiment it is 2% or less, while in a further embodiment it is 1% w/w or less. The polymer is to be used in an amount of at least 0.01% w/w.

The weight ratio of hydrophobically modified polymer to viscoelastic surfactant is usually from 0.1:100, preferably from 1:100, more preferably from 3:100, to 100:50, preferably to 100:100, more preferably to 50:100.

In addition to the surfactant and the specific hydrophobically modified polymer, a fluid of the invention may comprise further components. Typically an electrolyte is present in the fluid. For fracturing fluids typically one or more salts are present as the electrolyte, for example, inorganic salts such as the chlorides of ammonium, sodium, and potassium, and/or organic salts such as sodium salicylate are used. If used, salts are typically present in a concentration of 1-10% w/w, more preferably at a level of 3-4% w/w, based on the weight of the fracturing fluid. Alternatively, especially if the ground formation wherein the fracturing fluid is used contains a lot of such salts, the salt is not incorporated into the fluid when used, but picked up from said ground formation during the application.

The viscoelastic compositions of this invention may be used in other applications such as home and fabric cleaning, personal care, and agricultural applications. In these applications, the electrolyte will be different. For instance, in liquid detergents for laundry and automatic dishwashing, the electrolyte will take the form of builders. These builders include, but are not limited to, materials such as sodium carbonate, sodium sulfate, phosphate, silicate, citrate, and mixtures thereof. The electrolytes in agricultural applications may be water-soluble electrolytes used in pest control. Examples of these water-soluble electrolytes used in pest control include, but are not limited to, 2,4D salts, namely 2,4 dichlorophenoxy acetic acid salts with dimethylamine, glycolamine, and other amines, monochlorophenoxy acetic acid (MCPA); sodium, potassium, and amine based salts, 3,6-dichloro-2-methoxybenzoic acid (Dicamba); sodium, potassium, and amine based salts, 2-amino-4-(hydroxymethylphosphinyl) butanoic acid, ammonium salt (Glufosinate ammonium), sodium 5-[2-chloro-4-(trifluoromethyl)phenoxy]-2-nitro-benzoate (Acifluorfen-sodium), 2-chloro-N,N,N-trimethylethanaminium chloride (Chlormequat chloride), dichlorprop-2-(2,4-dichlorophenoxy)propanoate acid; sodium, potassium, and amine salts and others. In these applications, the electrolyte may be at a minimum of 1 wt % or more preferably at a minimum of 5 wt % and most preferably at a minimum of 10 wt % of the formulation. Furthermore, in these applications the electrolyte may be at a maximum of 90 wt % or more preferably at a maximum of 60 wt % and most preferably at a maximum of 40 wt % of the formulation.

The viscoelastic compositions of the invention may also comprise one or more chelating agents. Particularly when there are a lot of hardness ions in the aqueous formulations or the area where the compositions are used, the use of chelating agents for such ions was found to be beneficial. Without being bound by theory, it is thought that these hardness ions tend to precipitate the hydrophobically modified polymer in the aqueous solution. The addition of chelating agents, according to said theory, prevents the precipitation of these hydrophobically modified polymers and preserves the performance of the mixture of these polymers and viscoelastic surfactants in high hardness aqueous solutions. For purposes of this invention, a chelating agent is described as any material that will chelate hardness ions, such as calcium and magnesium, in aqueous solutions. Chelating agents include, but are not limited to, (S,S)-ethylenediaminesuccinic acid trisodium salt, N,N-bis(carboxymethyl)-L-glutamic acid tetrasodium salt, L-aspartate-(N,N)-diacetic acid tetrasodium salt, N-2-hydroxyethyliminodiacetic acid disodium salt, methylglycinediacetic acid trisodium salt, ethylenediaminetetraacetic acid, nitorilotriacetic acid, diethylenetriaminepentaacetic acid, hydroxyethylethylenediaminetriacetic acid, triethylenetetraminehexaacetic acid, 1,3-propanediaminetetraacetic acid, 1,3-diamino-2-hydroxypropanetetraacetic acid, dihydroxyethylglycine, glycol ether diaminetetraacetic acid, hydroxyethanediphosphonic acid, aminotrimethylenephosphonic acid, 1,2,4-butanetricarboxylic acid, dihydroxyethylethylenediaminediacetic acid, sodium gluconate, sodium glucoheptonate, inositol hexaphosphate, hydroxyethanoic acid, 2-hydroxypropanoic acid, 2-hydroxysuccinic acid, 2,3-dihydroxybutanedioic acid, and 2-hydroxy-1,2,3-propanetricarboxylic acid and their salts. The preferred chelating agents are aminocarboxylates such as, (S,S)-ethylenediaminesuccinic acid trisodium salt, N,N-bis(carboxymethyl)-L-glutamic acid tetrasodium salt, L-aspartate-(N,N)-diacetic acid tetrasodium salt, N-2-hydroxyethyliminodiacetic acid disodium salt, methylglycinediacetic acid trisodium salt, ethylenediaminetetraacetic acid, nitrilotriacetic acid, and their salts. For purposes of this invention, a high hardness aqueous solution is defined as a solution with a hardness of greater than 100 ppm expressed as $CaCO_3$, more preferably greater than 250 ppm as $CaCO_3$, and most preferably greater than 500 ppm as $CaCO_3$.

The fluid may also contain an organic solvent such as, for example, isopropanol, glycol, which may be used to help dissolve the viscoelastic surfactant component. The fluid may also contain further additives, including fluid loss additives such as a mixture of starch and mica.

Due to the fact that a surfactant is used to form the micelles, the fluid of the invention is hydrocarbon-responsive, so that the structure breaks down on contact or mixing with hydrocarbons. Typically, upon contact with hydrocarbons spherical micelles are formed which no longer show viscoelastic properties.

Practically, all compounds of the fluid of the invention are blended together. If a low viscosity is needed, the fluid is subjected to a high shear rate, allowing, for instance, pumping of the fluid into a downhole/bore well.

With the exception of the information in the examples, or where otherwise indicated, all numbers or expressions referring to quantities of ingredients, reaction conditions, and the like used in the specification and claims are to be understood as modified in all instances by the term "about". Further, where numerical ranges are disclosed, they are meant to be continuous ranges that include every value between the minimum and maximum value as presented. Wt % and % w/w mean percent by weight.

The invention will now be further described in connection with the following Examples, which, however, are not intended to limit the scope thereof. Unless otherwise stated, all parts and percentages refer to parts and percentages by weight. All numbers given relate to the amount of active material. So if in the examples 10% w/w of a chemical is specified, then the amount to be used of the supplied product is to be increased if the product is supplied in a diluted form.

EXAMPLES

Except where indicated otherwise, the viscosity of samples has been determined over a broad shear rate range using a stress-controlled rheometer SR-5000 (from Rheometric Scientific, which is now TA Instruments). The sample was placed between two circular parallel plates of 25 mm or 40 mm in diameter and evaluated at a temperature of 25° C. Typically the initial stress was 0.5 Pa and the final stress was in the 150-400 Pa range, depending on the viscosity of the sample, with the lower final stress selected for samples with lower viscosity. In the linear sweep mode a stress increment of 0.5-2 Pa was applied.

Aromox® APA-TW is a commercial tallowalkylamidopropyl dimethyl amine oxide supplied by AkzoNobel.

POLYFLOS® HM 21 is a hydrophobically modified hydroxypropyl guar gum supplied by Lamberti spa, and was used as received. This polymer was used as a comparison for the polymers of the invention.

Preparation of Anionic Hydrophobically Modified Polymer R7-33-43

Synthesis of Behenyl Alcohol m-TMI Monomer 75 g of behenyl alcohol (available from Cognis) were melted and added to a reactor and heated to 95° C. and sparged with nitrogen for 4 hours to remove any water. The nitrogen sparge was discontinued and the reaction temperature lowered to 78° C. 0.3 g of monomethyl ether hydroquinone (MEHQ) inhibitor and 0.3 g of Stannous 2-ethylhexanoate (FASCAT® 2003 available from Arkema Inc, Philadelphia, Pa.) were then added to the reactor. 47.6 g of 3-isopropenyl-α,α-dimethylbenzyl isocyanate (m-TMI available from Cytec, Stamford, Conn.) were then slowly added to the reactor over a period of 30 minutes. A slight exotherm was observed which raised the temperature to 78 to 83° C. After the addition, the reactor was held at 80° C. for an additional 30 minutes. The final product was a liquid which cooled down to a solid at room temperature.

Synthesis of the Polymer R7-33-43

An initial charge of 40.8 g of water and 153.5 g of isopropyl alcohol was added to a 1 liter glass reactor. The reactor contents were heated to reflux (approximately 82 to 84° C.). In a separate beaker, 142 g of acrylic acid were warmed to 55° C. and then 60 g of the behenyl alcohol urethane of m-TMI of the previous step were added with stirring. This warm mixture was added to the reactor at reflux over a period of 2.5 hours. A solution of 1.9 g of sodium persulfate dissolved in 60 g of water was simultaneously added but over said period of 2.5 hours. The reaction temperature was maintained at about 85° C. for one hour. A scavenge feed (to minimize residual monomer) containing 0.175 g of sodium persulfate dissolved in 10 g of water was then added to the reactor over 30 minutes at 85° C. The reactor was then set up for distillation, which was carried out at increased temperature and/or reduced pressure, to ensure a controlled distillation without polymer degradation. A small amount of ANTIFOAM® 1400 (0.12 g) (from Dow Chemical) was added to suppress any foam generated during distillation. The alcohol (the cosolvent) was removed from the polymer solution by azeotropic distillation. During the distillation, about 1350 g of water were added. Approximately, 263 g of a mixture of water and isopropyl alcohol were distilled off. After distillation was completed, the reaction mixture was cooled and 21.8 g of 50% NaOH were added. The final product had a pH of 2.2 and solids of 13.3 percent.

Preparation of Anionic Hydrophobically Modified Polymer R7-33-61

Synthesis of Armeen 18D m-TMI Monomer 70 g of octadecylamine (Armeen® 18D available from AkzoNobel Surface Chemistry) were melted and added to a reactor and heated to 90° C. The liquid octadecylamine was sparged with nitrogen for 4 hours to remove any water in the material. The nitrogen sparge was discontinued and the reaction temperature lowered to 78° C. 0.3 g of monomethyl ether hydroquinone (MEHQ) inhibitor and 0.3 g of Stannous 2-ethylhexanoate (FASCAT® 2003 available from Arkema Inc, Philadelphia, Pa.) were then added to the reactor. 52.2 g of 3-isopropenyl-α,α-dimethylbenzyl isocyanate (m-TMI available from Cytec, Stamford, Conn.) were then slowly added to the reactor over a period of 45 minutes. A slight exotherm was observed which raised the temperature to 80 to 83° C. After the addition, the reactor was held at 80° C. for an additional 30 minutes. The final product was a liquid which cooled down to a solid at room temperature.

Synthesis of the Polymer R7-33-61

An initial charge of 38 g of water and 150 g of isopropyl alcohol was added to a 1 liter glass reactor. The reactor contents were heated to reflux (approximately 82 to 84° C.). In a separate beaker, 142 g of acrylic acid were warmed to 55° C. and then 58.4 g of the Armeen 18D m-TMI monomer were added with stirring. This warm mixture was added to the reactor at reflux over a period of 2.5 hours. A solution of 1.9 g of sodium persulfate dissolved in 61 g of water was simultaneously added but over a period of 2.5 hours. The reaction temperature was maintained at about 85° C. for one hour. A scavenge feed containing 0.17 g of sodium persulfate dissolved in 10 g of water was then added to the reactor over 30 minutes at 85° C. The reactor was then set up for distillation. A small amount of ANTIFOAM® 1400 (0.12 g) (from Dow Chemical) was added to suppress any foam generated during distillation. The alcohol cosolvent was removed from the polymer solution by azeotropic distillation. During the distillation, about 1080 g of water were added. Approximately 251 g of a mixture of water and isopropyl alcohol were distilled off. After distillation was completed, the reaction mixture was cooled. The final product had a pH of 2.5 and solids of 15.7 percent.

Preparation of Anionic Hydrophobically Modified Polymer R7-36-72

Synthesis of 2-Decyl-Tetradecanol m-TMI Monomer 150 g of 2-decyl-tetradecanol (branched alcohol) [Isofol® 24 (97.5%) (available from Sasol, Houston, Tex.)] were added to a 500 ml reactor and heated to 80° C. The reactor contents were sparged with nitrogen for 4 hours to remove any water in the material. The nitrogen sparge was discontinued and the reaction temperature lowered to 68° C. 0.33 g of monomethyl ether hydroquinone (MEHQ) inhibitor and 0.33 g of Stannous 2-ethylhexanoate (FASCAT 2003 available from Arkema Inc, Philadelphia, Pa.) were then added to the reactor. 82.5 g of 3-isopropenyl-α,α-dimethylbenzyl isocyanate (m-TMI available from Cytec, Stamford, Conn.) were then slowly added to the reactor over a period of 30 minutes. A slight exotherm was observed which raised the temperature to 70 to 71° C. After the addition, the reactor was held at 72° C. for an additional 60 minutes. The final product was a liquid.

Synthesis of the Polymer R7-36-72

An initial charge of 43 g of water and 133 g of isopropyl alcohol was added to a 1 liter glass reactor. The reactor contents were heated to reflux (approximately 82 to 84° C.). A first monomer solution of 33 g of acrylic acid, 20.11 g of 2-decyl-tetradecanol m-TMI monomer (synthesized above), 9.9 g of isopropyl alcohol, and 4.1 g of hydroxypropyl methacrylate was added to the reactor at reflux over a period of 75 minutes. A second monomer solution containing 12.8 g of 50% 2-acrylamido-2-methyl propane sulfonic acid, sodium salt in 20 g of water was added concurrently over a period of 75 minutes. An initiator solution of 0.97 g of sodium persulfate dissolved in 28.3 g of water was simultaneously added but over a period of 90 minutes. The reaction temperature was maintained at about 85° C. for one hour. A scavenge feed containing 0.15 g of sodium persulfate dissolved in 10 g of water was then added to the reactor over 30 minutes at 85° C. The reactor was then set up for distillation and a small amount of ANTIFOAM® 1400 (0.12 g) (from Dow Chemical) was added to suppress any foam generated during distillation. The alcohol cosolvent was removed from the polymer solution by azeotropic distillation. Approximately 185 g of a mixture of water and isopropyl alcohol were distilled off. During the distillation, about 242 g of water were added to replace the distillate and keep the viscosity at a manageable level. After distillation was completed, the reaction mixture was cooled and 7 g of 50% NaOH in 15 g of water were added. The final product had a pH of 4.2 and solids of 16.9 percent.

Preparation of Polymer R7-33-158

An initial charge of 77 g of water and 100 g of isopropanol were added to a 1 liter glass reactor. The reactor contents were heated to 82° C. A first solution which is a mixture of 72.7 g of acrylic acid and 21.6 g of an N-octadecyl acrylamide dissolved in 50 g of isopropanol was added to the reactor over a period of 80 minutes. A second solution of 0.97 g of sodium persulfate dissolved in 46 g of water was simultaneously added at the same time but over a period of 90 minutes. After the second solution addition was completed, a solution of 0.09 g of sodium persulfate dissolved in 14 g of water was then added over a period of 10 minutes. The reactor was then set up for distillation. The alcohol cosolvent was removed from the polymer solution by azeotropic distillation. During the distillation, 450 g of water was dripped in and approximately, 303 g of a mixture of water and alcohol were distilled off. The final product was a clear colorless viscous solution with a pH of 2.6 and a solids content of 19.9%.

Preparation of Polymer R7-33-28

An initial charge of 72.9 g of water and 50.9 g of ethanol were added to a 500 ml glass reactor. The reactor contents were heated to reflux (approximately 82 to 84° C.). A mixture of 38.1 g of acrylic acid and 5.55 g of lauryl methacrylate was added to the reactor at reflux over a period of 3 hours. A solution of 0.6 g of sodium persulfate dissolved in 32 g of water was simultaneously added but over a period of 4 hours. The reaction temperature was maintained at about 85° C. for 30 minutes. The reactor was then set up for distillation. The alcohol cosolvent was removed from the polymer solution by azeotropic distillation. During the distillation, 38.8 g of 50% NaOH dissolved in 70 g of water was dripped in added. Approximately, 99.3 g of a mixture of water and ethanol were distilled off. The final product has 25.25% solid and pH=7.5.

Preparation of Polymer J3-9-46

An initial charge of 150 g diallyldimethylammonium chloride (65% Aldrich commercial material further concentrated to 88% by removal of water), 150 g isopropyl alcohol, and 32.2 g 2-decyl-tetradecanol m-TMI monomer (synthesized above) was added to a 1 liter glass reactor fitted with a condenser for reflux. An initiator feed consisting of Esperox 28 in isopropyl alcohol (16.4 g in a total volume of 100 mL) was prepared. The reaction was maintained in the range of 83 to 87° C., to allow for reflux of IPA, while the initiator solution was added over a period of 2 hr. Following the initiator slow addition, the reaction was maintained at 83° C. (refluxing IPA) for 2.5 hours. The reaction was cooled below the reflux temperature, and the reactor was then fitted with a Dean-Stark trap to allow for collection and removal of distillate. IPA/water was removed from 81 to 86° C. while the reaction volume was replenished with water from an addition funnel to maintain an acceptable viscosity. Total distillate collection up to this point was 194 g, while the added water was 350 g. Because of intense foaming, 195 g additional water was added to the reaction, and the reaction mixture was then transferred to a Roto-Vap apparatus, where an additional 110 g of distillate was removed under vacuum at 55° C. The weight of the final material after being subjected to distillation was 690 g. This was a pink-tinted, lightly cloudy liquid with a pH of 4 and consisting of 23% active polymer by weight.

The following Table 1 shows the molecular weights of some of the polymers tested in the experiments below. The molecular weights were measured as described in this document.

TABLE 1

Analysis of the hydrophobically modified polymers compared with the conventional POLYFLOS ® HM 21.

|  | R7-33-43 | R7-33-61 | R7-36-72 | R7-33-28 | R7-33-158 | POLYFLOS ® HM 21 |
|---|---|---|---|---|---|---|
| $M_w$ (Da) | 16131 | 19775 | 8459 | 29956 | 19528 | 537550 |
| $M_n$ (Da) | 2735 | 3199 | 1488 | 4095 | 2750 | 13641 |
| Dispersity = $M_w/M_n$ | 5.9 | 6.2 | 5.7 | 7.3 | 7.1 | 39.4 |

Example 1 and Comparative examples A-B

Rheology of Aromox APA-TW and hydrophobically modified polymer R7-33-43

Samples A, B, and 1 were made based on the amount shown in Table 2.

TABLE 2

Sample Preparation of Aromox APA-TW + R7-33-43

| Ex. | Description | Wt of Polymer (g) | Wt. of Aromox APA-TW (g) | Wt of 4% KCl Solution (g) | pH |
|---|---|---|---|---|---|
| A | 3 wt % (active) Aromox APA-TW, no polymer, in 4% KCl | None | 2.1270 | 27.9093 | 9.72 |
| B | 0.2 wt % (active) R7-33-43, no surfactant, in 4% KCl | 0.4956 | None | 29.7272 | 11.56 |
| 1 | 3 wt % (active) Aromox APA-TW + 0.2 wt % (active) R7-33-43, in 4% KCl | 0.4502 | 2.0939 | 27.5104 | 10.30 |

For samples A, B and 1, a strain-controlled rheometer ARES (from Rheometric Scientific, which is now TA Instruments) was used to conduct the Steady Strain Rate Sweep at 25° C., with an initial strain rate of 0.01 s$^{-1}$ and a final strain rate of 100 s$^{-1}$. Data was collected, 10 data points per strain rate decade. Parallel plates of diameter of 25 mm were used, and temperature was controlled by peltier heating.

The rheology profile is graphed in FIG. 1. Clearly sample 1 shows significantly higher viscosity than sample A and sample B, indicating a synergistic viscosity increase achieved by combination of Aromox APA-TW and R7-33-43 polymer (a polymer with a urethane linkage) in 4% KCl. The same synergistic viscosity increase was also found at 50° C. and at 80° C.

In a separate rheology test at 25° C., a dynamic frequency of 10$^{-1}$ to 10$^2$ rad/s was used and for the solution of Example 1 G' was higher than G" over the whole range, indicating the solution showed viscoelastic behavior.

Example 2 and Comparative Examples C-D

Rheology of Aromox APA-TW and hydrophobically modified polymer R7-33-61

Samples C, D, and 2 were made based on the amount shown in Table 3.

TABLE 3

Sample Preparation of Aromox APA-TW + R7-33-61

| Ex. | Description | Wt of Polymer (g) | Wt. of Aromox APA-TW (g) | Wt of 4% KCl Solution (g) | pH |
|---|---|---|---|---|---|
| C | 3 wt % (active) Aromox APA-TW, no polymer, in 4% KCl | None | 2.1270 | 27.9093 | 9.72 |
| D | 0.2 wt % (active) R7-33-61, no surfactant, in 4% KCl | 0.3992 | None | 29.6257 | 11.25 |
| 2 | 3 wt % (active) Aromox APA-TW + 0.2 wt % (active) R7-33-61, in 4% KCl | 0.3834 | 2.0971 | 27.5424 | 10.00 |

For samples C, D and 2, a strain-controlled rheometer ARES (from Rheometric Scientific, which is now TA Instruments) was used to conduct the Steady Strain Rate Sweep at 25° C., with an initial strain rate of 0.01 s$^{-1}$ and a final strain rate of 100 s$^{-1}$. Data was collected, 10 data points per strain rate decade. Parallel plates of diameter of 25 mm were used, and temperature was controlled by peltier heating.

The rheology profile is graphed in FIG. 2. Again, sample 2 shows significantly higher viscosity than sample C and sample D, indicating a synergistic viscosity increase achieved by combination of Aromox APA-TW and R7-33-61 polymer (a polymer with a urea linkage) in 4% KCl. The same synergistic viscosity increase was also found at 50° C. and at 80° C.

In a separate rheology test at 25° C., a dynamic frequency of 10$^{-1}$ to 10$^2$ rad/s was used and for the solution of Example 2 G' was higher than G" over the whole range, indicating the solution showed viscoelastic behavior.

Comparative Examples E and F

Rheology of Aromox® APA-TW and POLYFLOS® HM 21.

Samples E and F were formulated as shown in Table 4.

TABLE 4

Sample Preparation of Aromox APA-TW + POLYFLOS ® HM 21

| Ex. | Description | Wt of Polymer (g) | Wt. of Aromox APA-TW (g) | Wt of 4% KCl Solution (g) | pH |
|---|---|---|---|---|---|
| E | 3 wt % (active) Aromox APA-TW, no polymer, 4% KCl | None | 2.1000 | 27.9326 | 11.27 |
| F | 3 wt % (active) Aromox APA-TW + 0.2 wt % (active) POLYFLOS ® HM 21 in 4% KCl | 0.0774 | 2.0985 | 27.8268 | 11.81 |

The rheology profile is graphed in FIG. 3. The result show that samples E and F overlay very well with each other, indicating no rheological synergy upon combination of POLYFLOS® HM 21 with Aromox APA-TW in 4% KCl.

It is pointed out that the polymer in accordance with the invention (R7-33-43 of Example 1) has a much lower molecular weight than the conventional thickener POLYFLOS® HM 21 of the Comparative example F, see the Table 1 above. Hence it is surprising to see that the use of conventional hydrophobic polymers does not lead to the viscosities observed when using polymers of the invention.

Examples 3 and 4 and Comparative Example G

Rheology of Aromox APA-TW, Polymer R7-33-43 and Polymer R7-33-61

Here the performance of an amine-oxide viscoelastic surfactant in combination with the hydrophobically modified polymers R7-33-43 and R7-33-61 was investigated for an aqueous environment containing 4% KCl at elevated temperature (93° C. (200° F.)) and at an elevated pressure (27.5 bar (400 psi)), to mimic oil-well-stimulation conditions. The amounts of surfactant and polymer used as well as the results obtained are presented in the following Table 5, with the viscosity being determined after two hours at shear rate of 100 s$^{-1}$, using a Grace M5600 rheometer at said pressure and temperature with rotor R1 and bob B5.

TABLE 5

Sample preparation of samples G, 3 and 4

| Ex. | Description | Wt of Polymer (g) | Wt. of Aromox APA-TW (g) | Wt of KCl solution (g) | pH | HTHP Viscosity at 93° C./2 hr (mPa * s) |
|---|---|---|---|---|---|---|
| G | 3 wt % (active) Aromox APA-TW, no polymer, in 4% KCl | 0.0000 | 6.9683 | 93.0322 | 10.58 | 12.49 |
| 3 | 3 wt % (active) Aromox APA-TW + 0.2 wt % (active) R7-33-43, in 4% KCl | 1.5275 | 7.1534 | 91.5231 | 11.72 | 210.84 |
| 4 | 3 wt % (active) Aromox APA-TW + 0.2 wt % (active) R7-33-61, in 4% KCl | 1.2661 | 6.9709 | 91.7554 | 10.68 | 82.35 |

Clearly, also in a KCl-containing aqueous formulation and at high temperature and pressure, the combination of viscoelastic surfactant and hydrophobically modified polymer according to the invention gave a very high viscosity, even when polymer used in a small amount and despite the low molecular weight of the polymer.

Example 5 and Comparative Examples H and I

Rheology of Aromox APA-TW and Polymer R-36-72

Here, the performance of an amine-oxide viscoelastic surfactant in combination with hydrophobically modified polymer R7-36-72 was investigated for an aqueous environment containing 4% w/w KCl and an amount of CaCl$_2$ of 2,776 ppm (0.2776% w/w) at 25° C. The amounts of surfactant and polymer used as well as the results obtained are presented in the Table 6.

TABLE 6

Sample preparation of samples H, I and 5

| Ex. | Description | Wt. of Polymer (g) | Wt. of Aromox APA-TW (g) | Wt. of 4% KCl (g) | pH |
|---|---|---|---|---|---|
| H | 3 wt % (active) Aromox APA-TW, no polymer, in brine of CaCl$_2$/KCl | 0.0000 | 2.0852 | 27.9146 | 10.91 |
| I | 0.2 wt % (active) R7-36-72, no Aromox APA-TW, in brine of CaCl$_2$/KCl | 0.3714 | 0.0000 | 29.6453 | 10.26 |
| 5 | 3 wt % (active) Aromox APA-TW + 0.2 wt % (active) R7-36-72, in brine of CaCl$_2$/KCl | 0.3857 | 2.1083 | 27.5273 | 10.06 |

The combination in accordance with the invention gave a higher viscosity than the use of the surfactant or polymer alone, showing the synergistic behavior, despite the low molecular weight of the polymer and the small quantity in which it was used, as is demonstrated in FIG. 4. Polymer R7-36-72 contained AMPS monomer that provided tolerance to Calcium brine.

Example 6 and Comparative Example J

Rheology of Aromox APA-TW and Polymer R-33-43 with EDTA

In these examples the experiment of Example 5 was repeated, except that hydrophobically modified polymer R7-33-43 was used, while also using the well-known chelate EDTA (Dissolvine NA) in the composition. Samples 6 and J were prepared according to the amount shown in Table 7.

TABLE 7 sample preparation, samples 6 and J

| Ex. | Description | Wt. of Polymer R7-33-43 (g) | Wt. of Aromox APA-TW (g) | Wt. of Dissolvine NA (EDTA) (g) | Wt. of Brine (g) | pH |
|---|---|---|---|---|---|---|
| J | 3 wt % (active) Aromox APA-TW + EDTA, no polymer, in brine of CaCl$_2$/KCl | 0.0000 | 2.0917 | 0.3356 | 27.5758 | 9.93 |
| 6 | 3 wt % (active) Aromox APA-TW + 0.2 wt % (active) R7-33-43 + EDTA, in brine of CaCl$_2$/KCl | 0.4624 | 2.0940 | 0.3320 | 27.1467 | 9.80 |

FIG. 5 shows the viscosity of these formulations.

The results show that the combination of viscoelastic surfactant and low molecular weight hydrophobically modified polymer gives exceptionally high viscosity at low concentrations also in the presence of a chelate.

Example 7 and Comparative Example K

Rheology of Aromox APA-TW and Polymer R7-33-158

Samples 7 and K were prepared according to the amounts indicated in Table 8

TABLE 8

Preparation of samples 7 and K

| Ex. | Description | Wt. of Polymer R7-33-158 (g) | Wt. of Aromox APA-TW (g) | Wt. of 4% KCl (g) | pH |
|---|---|---|---|---|---|
| K | 3 wt % (active) Aromox APA-TW, no polymer, in 4% KCl | 0.0000 | 2.1270 | 27.9093 | 9.72 |
| 7 | 3 wt % (active) Aromox APA-TW + 0.2 wt % R7-33-158, in 4% KCl | 0.3026 | 2.1022 | 27.6135 | 12.06 |

For sample K, a strain-controlled rheometer ARES (from Rheometric Scientific, which is now TA Instruments) was used to conduct the Steady Strain Rate Sweep at 25° C., with an initial strain rate of 0.01 s$^{-1}$ and a final strain rate of 100 s$^{-1}$. Data was collected, 10 data points per strain rate decade. Parallel plates of diameter of 25 mm were used, and temperature was controlled by peltier heating.

FIG. 6 shows the viscosity of these samples. One can see from the overlap rheology profiles that the viscosity of sample 7 is higher than that of sample K in the shear rate range tested. The blend of Aromox APA-TW and polymer R7-33-158 (a polymer with an amide linkage between the pendant hydrophobe and the backbone) has higher viscosity than Aromox APA-TW alone.

Comparative Examples L and M

Rheology of Aromox APA-TW and Polymer R7-33-28

Samples L and M was prepared according to the amounts indicated in Table 9.

TABLE 9

Preparation of samples L and M

| Ex # | Description | Wt. of Polymer R7-33-28, (g) | Wt. of Aromox APA-TW (g) | Wt. of 4% KCl (g) | pH |
|---|---|---|---|---|---|
| L | 3 wt % (active) Aromox APA-TW, no polymer, in 4% KCl | 0.0000 | 2.1270 | 27.9093 | 9.72 |
| M | 3 wt % (active) APA-TW + 0.2 wt % (active) R7-33-28, in 4% KCl | 0.2335 | 2.1150 | 27.6778 | 8.71 |

For samples L and M, a strain-controlled rheometer ARES (from Rheometric Scientific, which is now TA Instruments) was used to conduct the Steady Strain Rate Sweep at 25° C., with an initial strain rate of 0.01 s$^{-1}$ and a final strain rate of 100 s$^{-1}$. Data was collected, 10 data points per strain rate decade. Parallel plates of diameter of 25 mm were used, and temperature was controlled by peltier heating.

FIG. 7 shows the viscosity of these samples. One can see from the overlap rheology profiles that the viscosity of sample M is lower than that of sample L. The blend of Aromox APA-TW and polymer R7-33-28 (a polymer with an ester linkage between the pendant hydrophobe and the backbone) has lower viscosity than Aromox APA-TW alone. In this case, blending VES and polymer showed a "negative" rheology synergy.

Example 8 and Comparative Example N

Viscoelasticity of Aromox APA-TW and Polymer R7-33-43

Samples 8 and N was prepared according to the amounts indicated in the following Table 10.

TABLE 10 preparation of samples 8 and N

| Ex # | Description | Wt. of Polymer (g) | Wt. of Aromox APA-TW (g) | Wt. of 4% KCl (g) | pH |
|---|---|---|---|---|---|
| N | 3 wt % (active) Aromox APA-TW, no polymer, in 4% KCl | 0.0000 | 2.1100 | 27.9126 | 10.17 |
| 8 | 3 wt % (active) Aromox APA-TW + 0.2 wt % (active) R7-33-43, in 4% KCl | 0.4585 | 2.0974 | 27.4362 | 9.26 |

Dynamic Frequency Sweep was tested using a stress-controlled rheometer SR-5000 (originally made by Rheometrics) at 25° C., with initial frequency of 0.01 rad/s and final frequency of 100 rad/s, and stress=1 Pa. Parallel plates of diameter of 40 mm were used, and temperature was controlled by peltier heating. 10 data points were collected within each decade of frequency.

The results are shown in FIGS. 8 and 9

From FIG. 8, one can see the significant difference of the G' and G" profile between the two samples. Sample N had no polymer, and its G', G" crossover frequency was roughly 3 rad/s. The sample showed viscoelasticity, or G'>G", only at frequencies that are higher than 3 rad/s. Sample 8 was the blend of Aromox APA-TW and polymer R7-33-43, and its G', G" crossover frequency was roughly 0.02 rad/s. The sample showed viscoelasticity, or G'>G", at frequencies that are higher than 0.02 rad/s. Therefore, the VES-polymer blend showed much wider frequency range where viscoelastcity was demonstrated.

From FIG. 9, one can see the significant difference in the phase angle between these two samples. Sample N had no polymer, and its phase angle is mostly higher than 45 degrees. Its phase angle was only below 45 degrees at frequency higher than 3 rad/s, indicating that it only has viscoelastic characteristics at frequencies higher than 3 rad/s. Sample 8 was the blend of Aromox APA-TW and polymer R7-33-43, and its phase angle was below 45 degrees at frequencies higher than 0.02 rad/s. This is another data to support that the VES-polymer blend is more viscoelastic than VES alone.

Example 9 and Comparative Example O

Viscoelasticity of Aromox APA-TW and Polymer J3-9-46

Samples 9 and O were prepared according to the amounts indicated in the following Table 11.

TABLE 11

Preparation of samples 9 and O

| Ex. | Description | Wt. of Polymer (g) | Wt. of Aromox APA-TW (g) | Wt. of 4% KCl (g) | pH Measured |
|---|---|---|---|---|---|
| O | 3 wt % (active) Aromox APA-TW, no polymer, in 4% KCl | 0.0000 | 2.1270 | 27.9093 | 9.72 |
| 9 | 3 wt % (active) Aromox APA-TW + 0.2% (active) J3-9-46, in 4% KCl | 0.4505 | 3.5028 | 46.0249 | 7.75 |

For sample O, a strain-controlled rheometer ARES (from Rheometric Scientific, which is now TA Instruments) was used to conduct the Steady Strain Rate Sweep at 25° C., with an initial strain rate of 0.01 s$^{-1}$ and a final strain rate of 100 s$^{-1}$. Data was collected, 10 data points per strain rate decade. Parallel plates of diameter of 25 mm were used, and temperature was controlled by peltier heating.

FIG. 10 shows the results from these experiments. For sample O, a strain-controlled rheometer ARES (from Rheometrics, which is now TA Instrument) was used to conduct the Steady Strain Rate Sweep at 25° C., with an initial strain rate of 0.01 s$^{-1}$ and a final strain rate of 100 s$^{-1}$. Data was collected, 10 data points per strain rate decade. Parallel plates of diameter of 25 mm were used, and temperature was controlled by peltier heating. For sample 9, a stress-controlled rheometer SR-5000 (from Rheometrics, which is now TA Instrument) was used to conduct the Steady Stress Sweep at 25° C., with an initial stress of 0.1 Pa, a final stress of 40 Pa, and a linear stress increment of 0.5 Pa. Parallel plates of diameter of 40 mm were used, and temperature was controlled by peltier heating.

One can see from the overlap rheology profiles that the viscosity of sample 9 is higher than that of sample O in the shear rate range tested. The blend of Aromox APA-TW and polymer J3-9-46 (a cationic hydrophobically modified polymer) has higher viscosity than Aromox APA-TW alone.

Example 10

Anionic/Betaine Surfactant-Polymer Dilution Experiments

Sodium lauryl ether sulfate and cocamidopropyl betaine were chosen as exemplary surfactants. They were used in a constant ratio to each other of 4:1 respectively. A series of eight dilution experiments were conducted. The compositions of the two series of experiments are found in Table 12 shown below. Sodium Chloride was the salt used in all the samples in Example 10. The first four dilution experiments (labeled 1-4) represent "no polymer controls". The latter four dilution experiments (labeled 5-8) contain different levels of a polymer R7-36-72 of the current invention. Columns A-D represent fixed levels of surfactant (column A for 15% surfactant, B for 10% surfactant, C for 7.5% surfactant, and D for 6% surfactant). In Table 13, the zero shear viscosities are shown to correlate with the dilution experiments described in Table 12.

TABLE 12

| | A Mass % Initial Sample | B Mass % First Dilution | C Mass % Second Dilution | D Mass % Third Dilution |
|---|---|---|---|---|
| 1 | | | | |
| % Surfactant | 15 | 10 | 7.5 | 6 |
| % Salt | 8 | 5.33 | 4 | 3.2 |
| % Water | 77 | 84.67 | 88.5 | 90.8 |
| 2 | | | | |
| % Surfactant | 15 | 10 | 7.5 | 6 |
| % Salt | 6 | 4 | 3 | 2.4 |
| % Water | 79 | 86 | 89.5 | 91.6 |
| 3 | | | | |
| % Surfactant | 15 | 10 | 7.5 | 6 |
| % Salt | 3 | 2 | 1.5 | 1.2 |
| % Water | 82 | 88 | 91 | 92.8 |
| 4 | | | | |
| % Surfactant | 15 | 10 | 7.5 | 6 |
| % Salt | 2 | 1.33 | 1 | 0.8 |
| % Water | 83 | 88.67 | 91.5 | 93.2 |
| 5 | | | | |
| % Surfactant | 15 | 10 | 7.5 | 6 |
| % Salt | 8 | 5.33 | 4 | 3.2 |
| % Polymer | 0.4 | 0.267 | 0.2 | 0.159 |
| % Water | 76.6 | 84.403 | 88.3 | 90.641 |
| 6 | | | | |
| % Surfactant | 15 | 10 | 7.5 | 6 |
| % Salt | 6 | 4 | 3 | 2.4 |
| % Polymer | 0.4 | 0.267 | 0.2 | 0.159 |
| % Water | 78.6 | 85.733 | 89.3 | 91.44 |
| 7 | | | | |
| % Surfactant | 15 | 10 | 7.5 | 6 |
| % Salt | 3 | 2 | 1.5 | 1.2 |
| % Polymer | 0.4 | 0.267 | 0.2 | 0.159 |
| % Water | 80.6 | 87.06 | 90.3 | 92.241 |
| 8 | | | | |
| % Surfactant | 15 | 10 | 7.5 | 6 |
| % Salt | 2 | 1.33 | 1 | 0.8 |
| % Polymer | 0.4 | 0.267 | 0.2 | 0.159 |
| % Water | 82.6 | 88.403 | 91.3 | 93.041 |

TABLE 13

Zero Shear Viscosity (Pa * s) - Surfactant + Polymer R7-36-72

| Experiment # | A | B | C | D |
|---|---|---|---|---|
| 1 | 0.004 | 54 | 115 | 16 |
| 2 | 6 | 173 | 31 | 0.4 |
| 3 | 130 | 157 | 0.7 | 0.007 |
| 4 | 0.001 | 0.001 | 0.001 | 0.001 |
| 5 | 0.7 | 22 | 170 | 58 |
| 6 | 1.3 | 188 | 138 | 1.7 |
| 7 | 31 | 492 | 5.4 | 0.001 |
| 8 | 209 | 17 | 0.001 | 0.001 |

Comparisons to determine influence of polymer at different salt levels can be made between the dilution experiment pairs of 1 and 5, 2 and 6, 3 and 7, and 4 and 8.

Zero Shear Viscosity

Zero shear viscosities were obtained from either a plot of viscosity vs. shear rate or fitting the data to Cross model. Viscosities were measured using a stress-controlled rheometer SR-5000 (from Rheometric Scientific, which is now TA Instruments) a stress controlled rheometer utilizing a 25 mm diameter parallel plate configuration and 1 mm gap. Steady state stress sweep measurements were carried out at 25° C. a data at different shear rate were obtained.

The zero shear viscosity was obtained by averaging the values at the viscosity plateau at the lower end of the shear rate range. For cases when the value does not reach plateau, the data was fitted to the Cross model. The fitting was carried out using the solver module of the Microsoft Excel software and setting the criterion to minimize the sum of the percentage differences between the observed and fitted data. According to the Cross model viscosity is related to shear rate by the following equation:

$$\eta = \eta_\infty + \frac{\eta_0 - \eta_\infty}{1 + (C\dot{\gamma})^m}$$

$\eta_0$=zero shear viscosity, $\eta_\infty$=viscosity at very high rate, $\dot{\gamma}$=shear rate, C and m are constants.

In one experiment, where $\eta_\infty$ was measured to 0.0404 Pa*s, C was determined to be 0.01 and m was determined to be 0.97, resulting in $\eta_0$ being 0.41 Pa*s.

The plot in FIG. 11 displays the results of zero shear viscosity vs. % w/w salt (NaCl) for the 8 dilution experiments from example 10. In this case, experiments #5-8 relate to experiments employing R7-36-72 as the polymer of the present invention.

These data demonstrate that R7-36-72 can effectively increase the zero shear viscosity for the sodium lauryl ether sulfate/cocamidopropyl betaine mixture over all levels surfactant to levels higher than can be achieved without polymer. Additionally, it can generally be seen that the peak viscosity of the system can be achieved with lower salt levels than in the absence of the polymer of the present invention. Furthermore, it can be observed that the zero shear viscosity of a high surfactant containing system can be achieved at substantially lower surfactant content by the addition of the polymer of the present invention with the appropriate level of salt.

The peak viscosity achieved for each surfactant level is provided in Table 14 below. Peak viscosity refers to the highest viscosity achieved over the entire salt range that was tested.

TABLE 14

| R7-36-72 Testing in Surfactant System | Peak Zero Shear Viscosity (Pa * s) |
| --- | --- |
| 6% surfactant without polymer | 16 |
| 6% surfactant with polymer | 58 |
| 7.5% surfactant without polymer | 115 |
| 7.5% surfactant with polymer | 170 |
| 10% surfactant without polymer | 173 |
| 10% surfactant with polymer | 429 |
| 15% surfactant without polymer | 130 |
| 15% surfactant with polymer | 209 |

Comparing samples with and without polymer shows that in all cases, the addition of polymer enables higher zero shear viscosities. Additionally, comparing 15% surfactant without polymer (130 Pa*s) to 10% surfactant without polymer (173 Pa*s) and 10% surfactant with polymer (429 Pa*s) shows that it is possible to achieve higher zero shear viscosities with lower levels of surfactant by addition of the polymer of the present invention and the appropriate level of salt.

The invention claimed is:

1. An aqueous viscoelastic composition comprising
   a. at least one viscoelastic surfactant selected from the group consisting of amine oxide and amidoamine oxide surfactants,
   b. at least one hydrophobically modified polymer, which:
      i. is formed from polymerization of ethylenically unsaturated monomers;
      ii. has a number average molecular weight of from 1,000 to 90,000 Da;
      iii. to a level of at least 0.1 mole %, based on the amount of monomer units in the polymer, contains monomeric units each covalently bonded to a pendant, optionally alkoxylated, linear or branched hydrocarbyl group having from 6 to 40 carbon atoms, said pendant, optionally alkoxylated, linear or branched hydrocarbyl group being connected to the backbone of said hydrophobically modified polymer via a urea, urethane, imide or amide containing linking group, and
   c. a member selected from organic salts, inorganic salts, organic acid and organic acid salts.

2. A composition according to claim 1, wherein said pendant, optionally alkoxylated, hydrocarbyl group has at least 12 carbon atoms and said hydrophobically modified polymer to a level of from 0.1 to 20 mole % based on the amount of monomer units in the polymer, contains monomeric units connected to said pendant, optionally alkoxylated, hydrocarbyl group.

3. A composition according to claim 1, wherein said pendant, optionally alkoxylated, hydrocarbyl group has at most 11 carbon atoms and said hydrophobically modified polymer to a level of from 1 to 50 mole % based on the amount of monomer units in the polymer, contains monomeric units connected to said pendant, optionally alkoxylated, hydrocarbyl group.

4. A composition according to claim 1, wherein said non-ester linking group is selected from the group consisting of urea, urethane, imide and amide containing linking groups and a direct bond.

5. A composition according to claim 1, wherein said pendant, optionally alkoxylated, hydrocarbyl group contains at least 8 carbon atoms.

6. A composition according to claim 1, wherein said pendant, optionally alkoxylated, hydrocarbyl group contains at most 32 carbon atoms.

7. A composition according to claim 1, wherein said pendant, optionally alkoxylated, hydrocarbyl group is a branched alkyl or alkenyl group.

8. A composition according to claim 1, wherein said hydrophobically modified polymer is present in a concentration below the overlap concentration of said polymer.

9. A composition according to claim 1, wherein said hydrophobically modified polymer is obtainable by copolymerizing at least a first and at least a second ethylenically unsaturated monomer, wherein
   a. said first monomer is an ethylenically unsaturated monomer with a optionally alkoxylated hydrocarbyl group having from 6 to 40 carbon atoms, being connected to the unsaturated function of said monomer via a non-ester containing linkage;
   b. said second monomer is an ethylenically unsaturated monomer free from hydrocarbyl groups having 6 or more carbon atoms connected to the unsaturated function of said monomer;
said first and second monomer being present in a mutual molar ratio of from 0.1:99.9 to 90:10.

10. A composition according to claim 9, wherein said optionally alkoxylated hydrocarbyl group has at least 12 carbon atoms and said first and second monomers are present in a molar ratio of from 0.1:99.9 to 20:80.

11. A composition according to claim 9, wherein said optionally alkoxylated hydrocarbyl group has at most 11 carbon atoms and said first and second monomers are present in a mutual molar ratio of from 1:99 to 90:10.

12. A composition according to claim 9, wherein said first ethylenically unsaturated monomer has the formula:

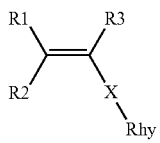

where
R1, R2, and R3 are independently selected from H, $CH_3$, COOH, and $CH_2COOH$,
Rhy is a straight or branched, saturated or unsaturated hydrocarbyl group having from 6, to 40 carbon atoms, which group optionally is alkoxylated,
X is a linking group selected from a direct bond or

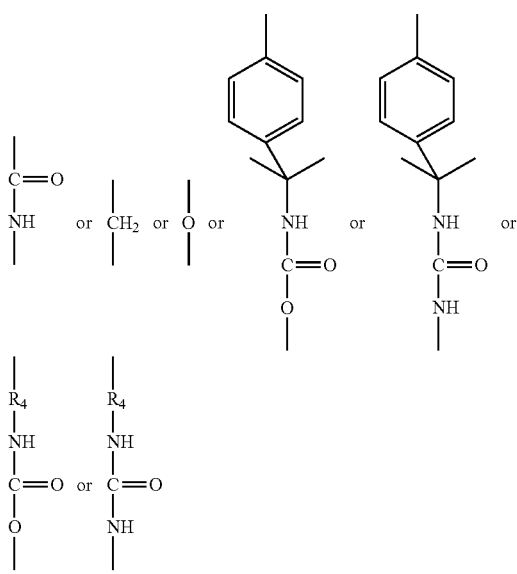

where R4 is a hydrocarbylene group having 1 to 10 carbon atoms, the top bond of X is linked to the double bond of the ethylenically unsaturated monomer and the bottom bond of X is linked to the group Rhy.

13. A composition according to claim 9, wherein said second ethylenically unsaturated monomer is selected from the group consisting of anionic ethylenically unsaturated monomers, cationic ethylenically unsaturated monomers, nonionically ethylenically unsaturated monomers, zwitterionic ethylenically unsaturated monomers, and mixtures thereof and salts thereof.

14. A composition according to claim 9, wherein said second ethylenically unsaturated monomer is selected from the group consisting of (meth)acrylic acid, maleic acid or maleic anhydride, itaconic acid, 2-acrylamido-2-methyl propane sulfonic acid, vinyl sulfonic acid, sodium methallyl sulfonate, sulfonated styrene, allyloxybenzene sulfonic acid and mixtures thereof and salts thereof.

15. A composition according to claim 1 wherein said hydrophobically modified polymer has a number average molecular weight of from 1,500 to 90,000 Da.

16. A composition according to claim 1, wherein a 2 wt % solution of said hydrophobically modified polymer in a 4 wt % KCl solution in water has a viscosity of at most 100 mPa*s, measured at 100 $sec^{-1}$ at a temperature of 25° C.

17. A composition according to claim 1, wherein the weight ratio of hydrophobically modified polymer to viscoelastic surfactant is from 0.1:100.

18. A composition according to claim 1, wherein the concentration of said hydrophobically modified polymer is from 0.01, by weight of the total composition.

19. A composition according to claim 1, wherein the concentration of said viscoelastic surfactant is from 0.1 to 50% by weight of the total composition.

20. A composition according to claim 1, further comprising solid particles dispersed therein.

21. A composition according to claim 1, wherein the concentration of said member is from 0.1 to 30% by weight of the total composition.

22. A composition according to claim 1, further comprising a chelating agent.

23. A method for fracturing a rock formation, comprising the steps of injecting the viscoelastic composition of claim 1 via a bore hole into said rock formation at a pressure sufficient to fracture said rock.

24. A method according to claim 23, wherein said rock formation is a subterranean rock formation, and said bore hole is a well bore.

25. A method for thickening a viscoelastic composition comprising a viscoelastic surfactant and a member selected from organic salts, inorganic salts, organic acid and organic acid salts, the method comprising the step of adding to the viscoelastic composition a hydrophobically modified polymer, which:
  a. is formed from polymerization of ethylenically unsaturated monomers;
  b. has a number average molecular weight of from 1,000 to 90,000 Da;
  c. to a level of at least 0.1 mole %, based on the amount of monomer units in the polymer, contains monomeric units each covalently bonded to a pendant, optionally alkoxylated, linear or branched hydrocarbyl group having from 6 to 40 carbon atoms, said pendant, optionally alkoxylated, linear or branched hydrocarbyl group being connected to the backbone of said hydrophobically modified polymer via a urea, urethane, imide or amide containing linking group.

26. A method for thickening a liquid composition selected from the group consisting of detergents, hard surface cleaners, fabric cleaners, and agricultural formulations, the method comprising the step of adding to the liquid composition the aqueous viscoelastic composition of claim 1.

27. A composition according to claim 1, wherein the viscoelastic surfactant is an amidoamine oxide surfactant.

* * * * *